(12) United States Patent
Scheller et al.

(10) Patent No.: US 9,226,854 B2
(45) Date of Patent: Jan. 5, 2016

(54) STEERABLE LASER PROBE

(71) Applicant: Katalyst Surgical, LLC, Chesterfield, MO (US)

(72) Inventors: Gregg D Scheller, Wildwood, MO (US); Matthew N Zeid, Ballwin, MO (US)

(73) Assignee: Katalyst Surgical, LLC, Chesterfield, MO (US)

( * ) Notice: Subject to any disclaimer, the term of this patent is extended or adjusted under 35 U.S.C. 154(b) by 0 days.

(21) Appl. No.: 14/676,080

(22) Filed: Apr. 1, 2015

(65) Prior Publication Data

US 2015/0202078 A1 Jul. 23, 2015

Related U.S. Application Data

(63) Continuation of application No. 13/861,090, filed on Apr. 11, 2013, now Pat. No. 9,023,019.

(51) Int. Cl.
*A61B 17/00* (2006.01)
*A61B 18/18* (2006.01)
*A61F 9/008* (2006.01)
*A61N 5/06* (2006.01)
(Continued)

(52) U.S. Cl.
CPC .............. *A61F 9/008* (2013.01); *A61F 9/00823* (2013.01); *A61B 18/22* (2013.01); *A61B 19/22* (2013.01); *A61B 2018/00589* (2013.01); *A61B 2018/225* (2013.01); *A61B 2018/2238* (2013.01); *A61F 9/00821* (2013.01); *A61F 2009/00863* (2013.01); *A61F 2009/00872* (2013.01); *A61N 5/062* (2013.01)

(58) Field of Classification Search
CPC ..... A61F 9/008; A61F 9/00821; A61B 18/22; A61B 19/22
USPC ..................................................... 606/1, 4, 15
See application file for complete search history.

(56) References Cited

U.S. PATENT DOCUMENTS 5,190,050 A 3/1993 Nitzsche
5,355,871 A 10/1994 Hurley et al.
(Continued)

FOREIGN PATENT DOCUMENTS

EP   EP 0900547 B1   3/1999
WO   WO 2006/091597 A1   8/2006

OTHER PUBLICATIONS

H. Fischer, B. Vogel, W. Pfleging, H. Besser, Flexible distal tip made of nitinol (NiTi) for a steerable endoscopic camera system, Materials Science and Engineering A273-275 (1999) 780-783.

*Primary Examiner* — Lynsey Crandall
*Assistant Examiner* — Sebastian X Lukjan
(74) *Attorney, Agent, or Firm* — Kevin P. Rollins

(57) ABSTRACT

A steerable laser probe may include a handle, an actuation structure of the handle, a housing tube, an optic fiber, and an optic fiber sleeve. The housing tube may have a first housing tube portion having a first stiffness and a second housing tube portion having a second stiffness. The second stiffness may be greater that the first stiffness. The optic fiber may be disposed within an inner bore of the handle, the optic fiber sleeve, the actuation structure, and the housing tube. The optic fiber sleeve may enclose at least a portion of the optic fiber and the optic fiber sleeve may be disposed within the actuation structure and the housing tube. A compression of the actuation structure may be configured to curve the housing tube and the optic fiber.

11 Claims, 28 Drawing Sheets

(51) Int. Cl.
*A61B 19/00* (2006.01)
*A61B 18/22* (2006.01)
*A61B 18/00* (2006.01)

(56) References Cited

U.S. PATENT DOCUMENTS

| | | | |
|---|---|---|---|
| 5,381,782 A | 1/1995 | DeLaRama et al. |
| 5,439,000 A | 8/1995 | Gunderson et al. |
| 5,454,794 A | 10/1995 | Narciso et al. |
| 5,520,222 A | 5/1996 | Chikama |
| 6,123,699 A | 9/2000 | Webster, Jr. |
| 6,126,654 A | 10/2000 | Giba et al. |
| 6,198,974 B1 | 3/2001 | Webster, Jr. |
| 6,488,695 B1 | 12/2002 | Hickingbotham |
| 6,505,530 B2 | 1/2003 | Adler et al. |
| 6,530,913 B1 | 3/2003 | Giba et al. |
| 6,551,302 B1 | 4/2003 | Rosinko et al. |
| 6,572,608 B1 | 6/2003 | Lee et al. |
| 6,620,153 B2 | 9/2003 | Mueller et al. |
| 6,730,076 B2 | 5/2004 | Hickingbotham |
| 6,863,668 B2 | 3/2005 | Gillespie et al. |
| 6,984,230 B2 | 1/2006 | Scheller et al. |
| 7,004,957 B1 | 2/2006 | Dampney et al. |
| 7,303,533 B2 | 12/2007 | Johansen et al. |
| 7,402,158 B2 | 7/2008 | Scheller et al. |
| 7,632,242 B2 | 12/2009 | Griffin et al. |
| 7,766,904 B2 | 8/2010 | Mc Gowan, Sr. et al. |
| 8,038,692 B2 | 10/2011 | Valencia et al. |
| 8,075,553 B2 | 12/2011 | Scheller et al. |
| 8,197,468 B2 | 6/2012 | Scheller et al. |
| 2003/0171762 A1 | 9/2003 | Forchette et al. |
| 2004/0181138 A1 | 9/2004 | Hindricks et al. |
| 2004/0249367 A1 | 12/2004 | Saadat et al. |
| 2005/0054900 A1 | 3/2005 | Mawn et al. |
| 2005/0157985 A1 | 7/2005 | McGowan, Sr. et al. |
| 2005/0272975 A1 | 12/2005 | McWeeney et al. |
| 2005/0277874 A1 | 12/2005 | Selkee |
| 2006/0178674 A1* | 8/2006 | McIntyre ............... 606/108 |
| 2007/0185514 A1 | 8/2007 | Kirchhevel |
| 2009/0018393 A1 | 1/2009 | Dick et al. |
| 2009/0187170 A1 | 7/2009 | Auld et al. |
| 2009/0312750 A1 | 12/2009 | Spaide |
| 2010/0004642 A1 | 1/2010 | Lumpkin |
| 2010/0268234 A1 | 10/2010 | Aho et al. |
| 2011/0028947 A1 | 2/2011 | Scheller et al. |
| 2012/0116361 A1 | 5/2012 | Hanlon et al. |
| 2013/0035551 A1 | 2/2013 | Yu et al. |
| 2013/0060240 A1 | 3/2013 | Scheller et al. |
| 2013/0071507 A1 | 3/2013 | Scheller et al. |
| 2013/0096541 A1 | 4/2013 | Scheller et al. |
| 2013/0116671 A1 | 5/2013 | Scheller et al. |
| 2013/0150838 A1 | 6/2013 | Scheller et al. |
| 2013/0165910 A1 | 6/2013 | Scheller et al. |
| 2013/0261610 A1 | 10/2013 | LaConte et al. |

* cited by examiner

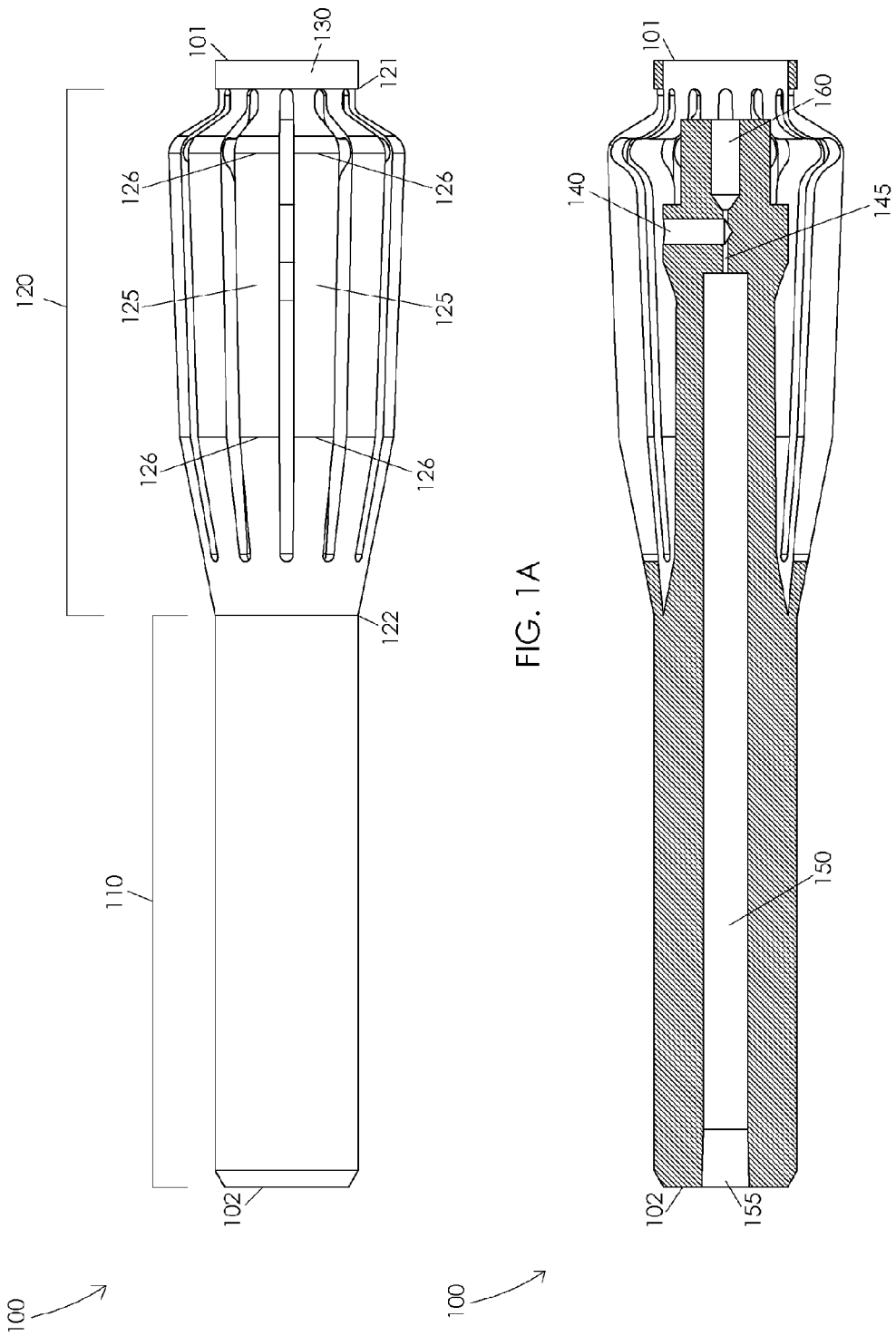

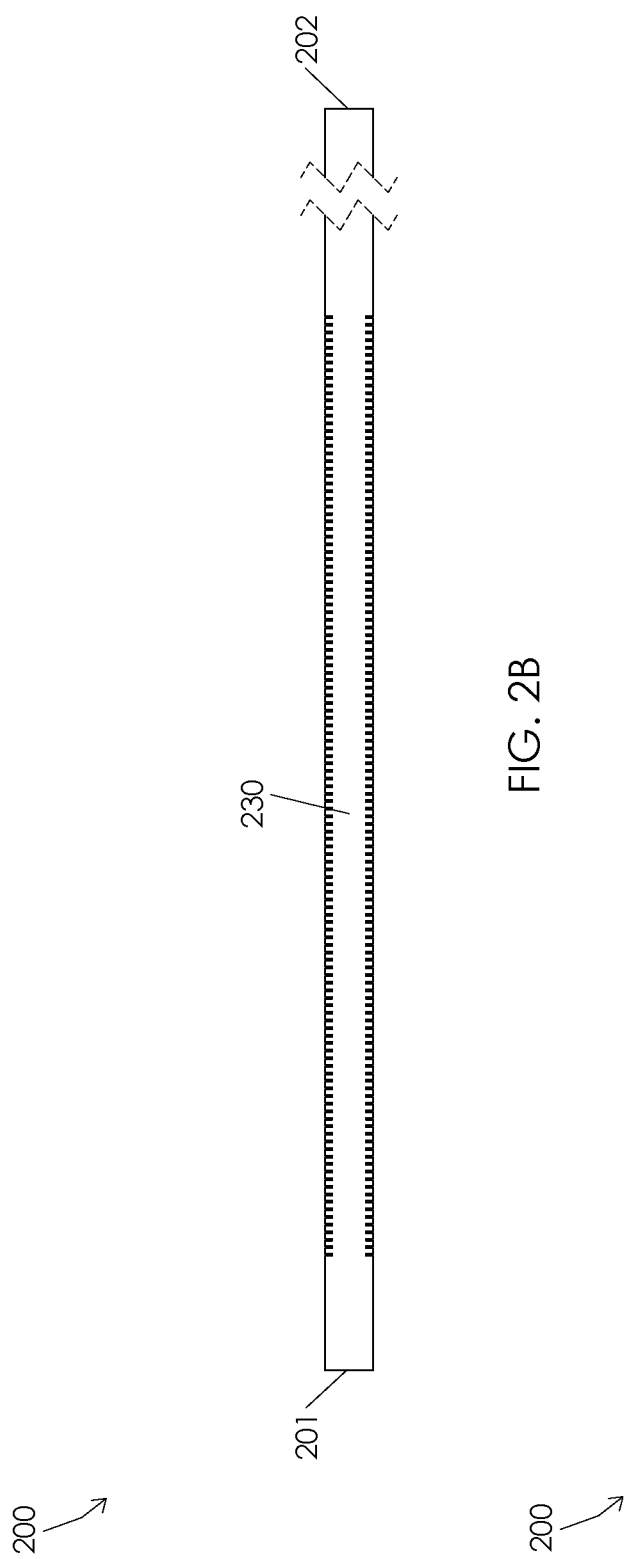

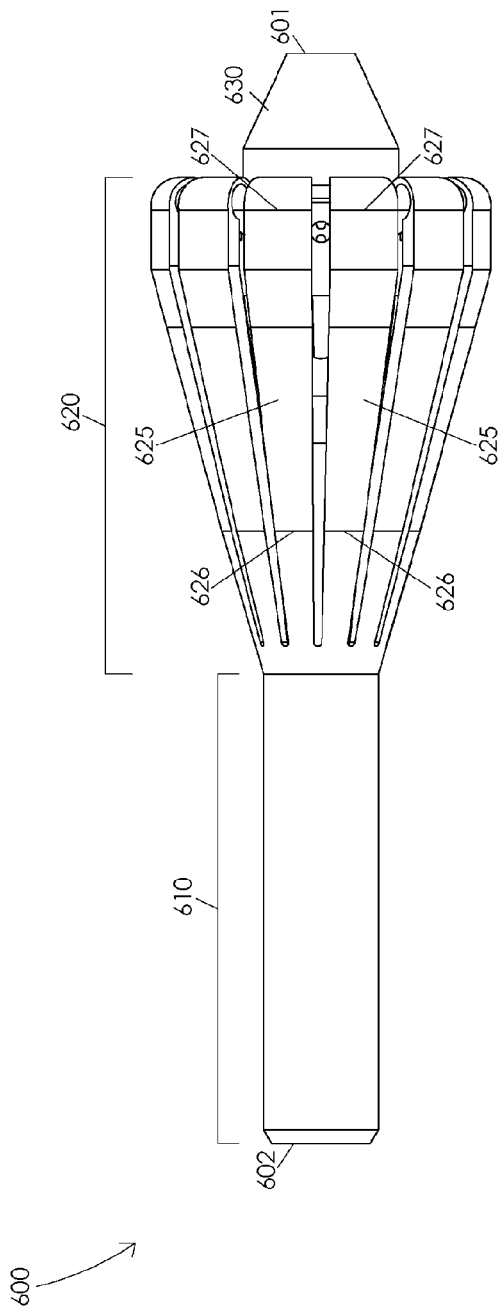
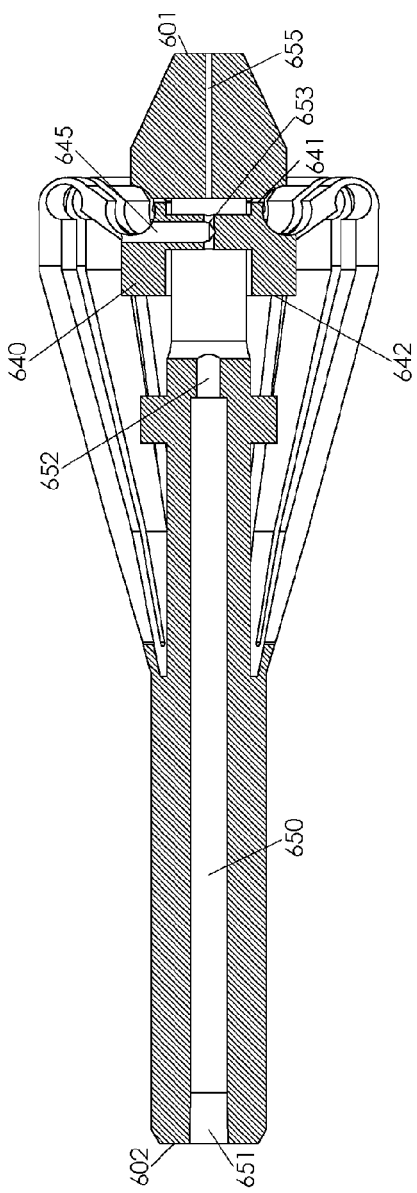
FIG. 6A
FIG. 6B

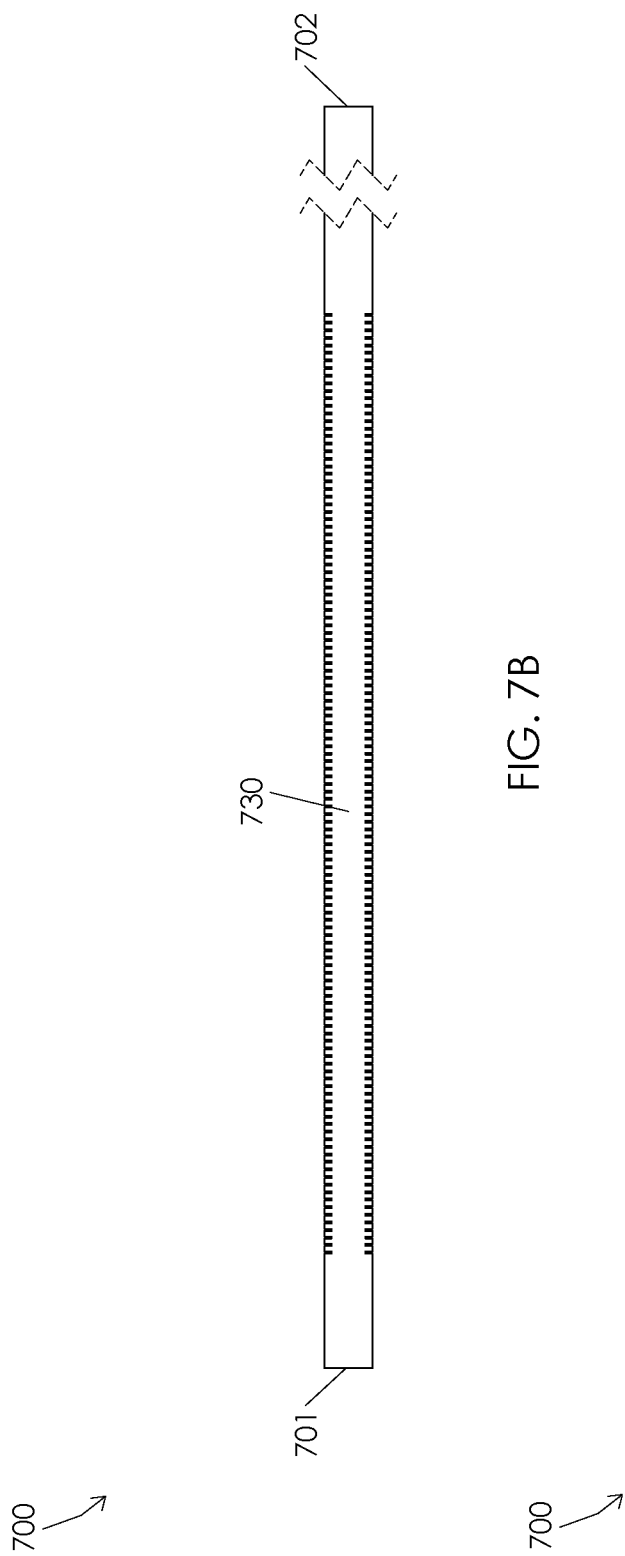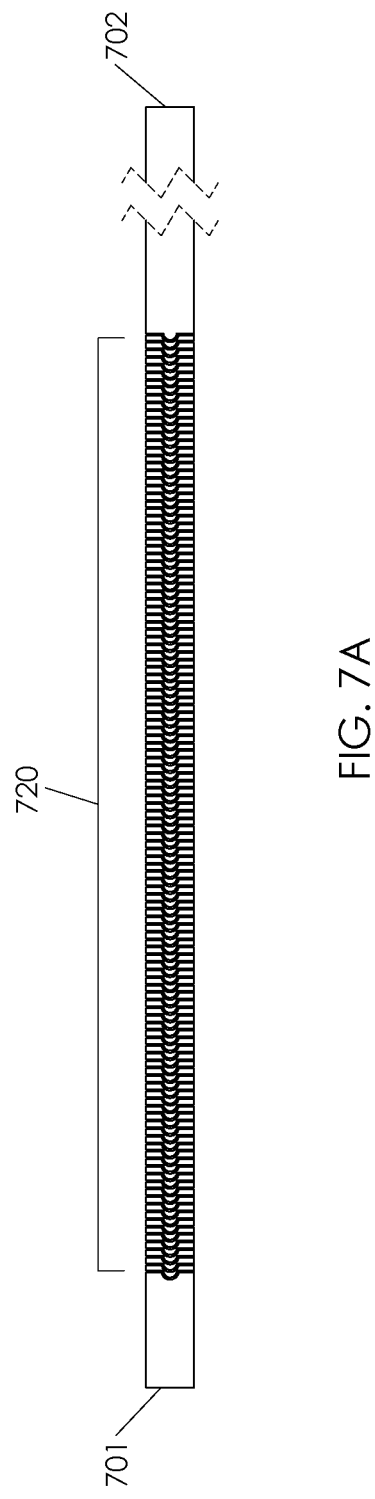

STEERABLE LASER PROBE

CROSS-REFERENCE TO RELATED APPLICATIONS

This Application is a continuation of prior application Ser. No. 13/861,090, filed Apr. 11, 2013.

FIELD OF THE INVENTION

The present disclosure relates to a surgical instrument, and, more particularly, to a steerable laser probe.

BACKGROUND OF THE INVENTION

A wide variety of ophthalmic procedures require a laser energy source. For example, ophthalmic surgeons may use laser photocoagulation to treat proliferative retinopathy. Proliferative retinopathy is a condition characterized by the development of abnormal blood vessels in the retina that grow into the vitreous humor. Ophthalmic surgeons may treat this condition by energizing a laser to cauterize portions of the retina to prevent the abnormal blood vessels from growing and hemorrhaging.

In order to increase the chances of a successful laser photocoagulation procedure, it is important that a surgeon is able aim the laser at a plurality of targets within the eye, e.g., by guiding or moving the laser from a first target to a second target within the eye. It is also important that the surgeon is able to easily control a movement of the laser. For example, the surgeon must be able to easily direct a laser beam by steering the beam to a first position aimed at a first target, guide the laser beam from the first position to a second position aimed at a second target, and hold the laser beam in the second position. Accordingly, there is a need for a surgical laser probe that can be easily guided to a plurality of targets within the eye.

BRIEF SUMMARY OF THE INVENTION

The present disclosure provides a steerable laser probe. In one or more embodiments, a steerable laser probe may comprise a handle, an actuation structure of the handle, a housing tube, an optic fiber, and an optic fiber sleeve. Illustratively, the housing tube may comprise a first housing tube portion having a first stiffness and a second housing tube portion having a second stiffness. In one or more embodiments, the second stiffness may be greater that the first stiffness. Illustratively, the optic fiber may be disposed within an inner bore of the handle, the optic fiber sleeve, the actuation structure, and the housing tube. In one or more embodiments, the optic fiber sleeve may enclose at least a portion of the optic fiber and the optic fiber sleeve may be disposed within the actuation structure and the housing tube.

In one or more embodiments, a compression of the actuation structure may be configured to extend the housing tube relative to the optic fiber sleeve causing the optic fiber sleeve to apply a compressive force to a portion of the housing tube. Illustratively, an application of a compressive force to a portion of the housing tube may be configured to compress a portion of the housing tube. In one or more embodiments, a compression of a portion of the housing tube may be configured to gradually curve the housing tube. Illustratively, a gradual curving of the housing tube may be configured to gradually curve the optic fiber.

In one or more embodiments, a decompression of the actuation structure may be configured to retract the housing tube relative to the optic fiber sleeve causing the optic fiber sleeve to reduce a compressive force applied to a portion of the housing tube. Illustratively, a reduction of a compressive force applied to a portion of the housing tube may be configured to decompress a portion of the housing tube. In one or more embodiments, a decompression of a portion of the housing tube may be configured to gradually straighten the housing tube. Illustratively, a gradual straightening of the housing tube may be configured to gradually straighten the optic fiber.

In one or more embodiments, a compression of the actuation structure may be configured to retract the optic fiber sleeve relative to the housing tube causing the optic fiber sleeve to apply a compressive force to a portion of the housing tube. Illustratively, an application of a compressive force to a portion of the housing tube may be configured to compress a portion of the housing tube. In one or more embodiments, a compression of a portion of the housing tube may be configured to gradually curve the housing tube. Illustratively, a gradual curving of the housing tube may be configured to gradually curve the optic fiber.

In one or more embodiments, a decompression of the actuation structure may be configured to extend the optic fiber sleeve relative to the housing tube causing the optic fiber sleeve to reduce a compressive force applied to a portion of the housing tube. Illustratively, a reduction of a compressive force applied to a portion of the housing tube may be configured to decompress a portion of the housing tube. In one or more embodiments, a decompression of a portion of the housing tube may be configured to gradually straighten the housing tube. Illustratively, a gradual straightening of the housing tube may be configured to gradually straighten the optic fiber.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 1A and 1B are schematic diagrams illustrating a handle;

FIGS. 2A, 2B, and 2C are schematic diagrams illustrating a housing tube;

FIGS. 6A and 6B are schematic diagrams illustrating a handle;

FIGS. 7A, 7B, and 7C are schematic diagrams illustrating a housing tube;

DETAILED DESCRIPTION OF AN ILLUSTRATIVE EMBODIMENT

Figure 2C:
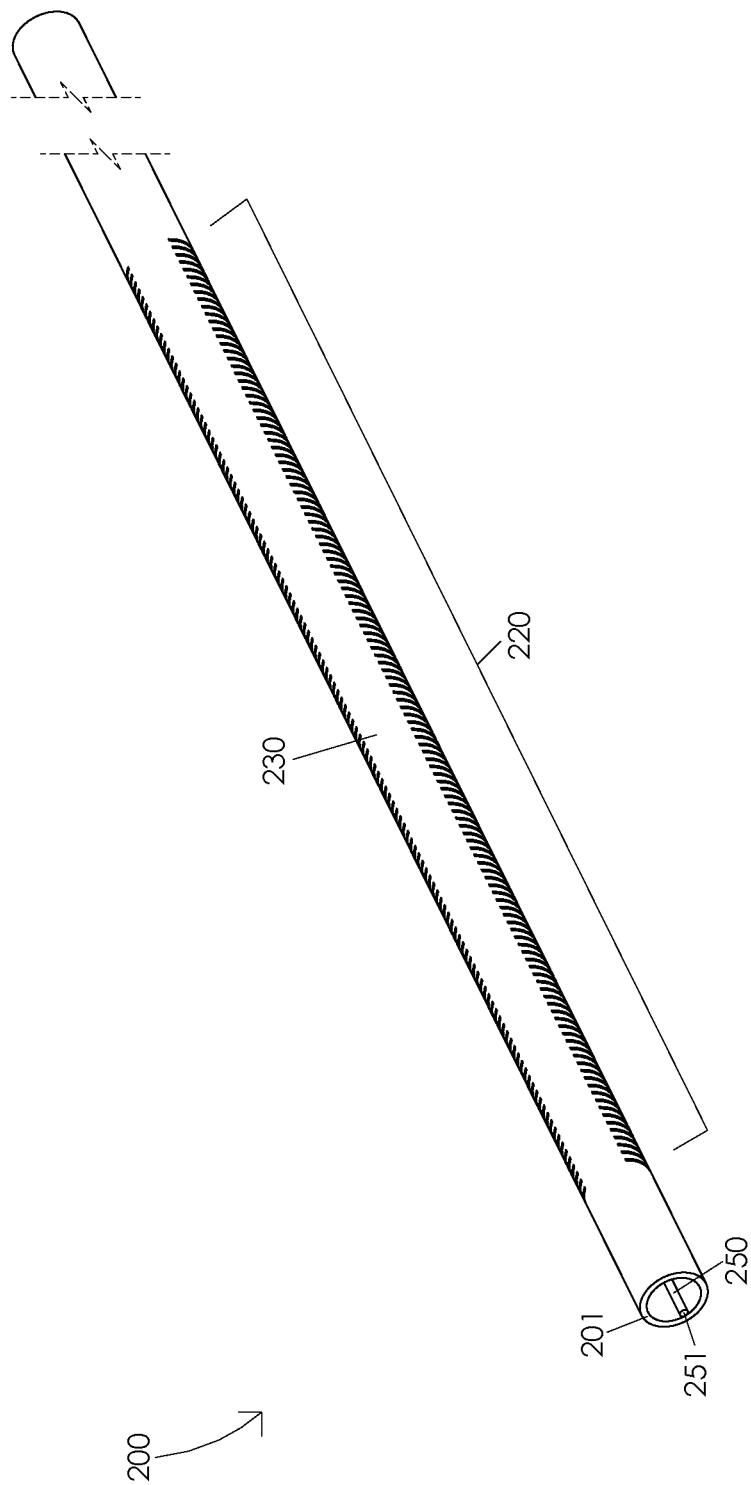

FIGS. 1A and 1B are schematic diagrams illustrating a handle 100. FIG. 1A illustrates a top view of handle 100. In one or more embodiments, handle 100 may comprise a handle distal end 101, a handle proximal end 102, a handle base 110, an actuation structure 120, and an actuation ring 130. Illustratively, actuation structure 120 may comprise an actuation structure distal end 121 and an actuation structure proximal end 122. In one or more embodiments, actuation structure 120 may comprise a plurality of actuation arms 125. Illustratively, each actuation arm 125 may comprise at least one extension mechanism 126. In one or more embodiments, actuation structure 120 may comprise a shape memory material configured to project actuation structure distal end 121 a first distance from actuation structure proximal end 122, e.g., when actuation structure 120 is fully decompressed. Illustratively, actuation structure 120 may comprise a shape memory material configured to project actuation structure distal end 121 a second distance from actuation structure proximal end 122, e.g., when actuation structure 120 is fully compressed. In one or more embodiments, the second distance from actuation structure proximal end 122 may be greater than the first distance from actuation structure proximal end 122. Actuation structure 120 may be manufactured from any suitable material, e.g., polymers, metals, metal alloys, etc., or from any combination of suitable materials.

Illustratively, actuation structure 120 may be compressed by an application of a compressive force to actuation structure 120. In one or more embodiments, actuation structure 120 may be compressed by an application of one or more compressive forces located at one or more locations around an outer perimeter of actuation structure 120. Illustratively, the one or more locations may comprise any of a plurality of locations around the outer perimeter of actuation structure 120. For example, a surgeon may compress actuation structure 120 by squeezing actuation structure 120. Illustratively, the surgeon may compress actuation structure 120 by squeezing actuation structure 120 at any particular location of a plurality of locations around an outer perimeter of actuation structure 120. For example, a surgeon may rotate handle 100 and compress actuation structure 120 from any rotational position of a plurality of rotational positions of handle 100.

In one or more embodiments, actuation structure 120 may be compressed by an application of a compressive force to any one or more of the plurality of actuation arms 125. Illustratively, each actuation arm 125 may be configured to actuate independently. In one or more embodiments, each actuation arm 125 may be connected to one or more of the plurality of actuation arms 125 wherein an actuation of a particular actuation arm 125 may be configured to actuate every actuation arm 125 of the plurality of actuation arms 125. Illustratively, one or more actuation arms 125 may be configured to actuate in pairs or groups. For example, an actuation of a first actuation arm 125 may be configured to actuate a second actuation arm 125.

In one or more embodiments, a compression of actuation structure 120, e.g., due to an application of a compressive force to a particular actuation arm 125, may be configured to actuate the particular actuation arm 125. Illustratively, an actuation of the particular actuation arm 125 may be configured to actuate every actuation arm 125 of the plurality of actuation arms 125. In one or more embodiments, an application of a compressive force to a particular actuation arm 125 may be configured to extend at least one extension mechanism 126 of the particular actuation arm 125. Illustratively, a particular actuation arm 125 may be configured to extend a first length from handle base 110. An extension of an extension mechanism 126 of the particular actuation arm 125, e.g., due to an application of a compressive force to the particular actuation arm 125, may be configured to extend the particular actuation arm 125 a second length from handle base 110. Illustratively, the second length from handle base 110 may be greater than the first length from handle base 110.

In one or more embodiments, actuation ring 130 may be fixed to actuation structure distal end 121. Illustratively, a compression of actuation structure 120 may be configured to gradually extend actuation ring 130 from handle base 110. For example, actuation ring 130 may be configured to extend a first distance from actuation structure proximal end 122, e.g., when actuation structure 120 is fully decompressed. Actuation ring 130 may be configured to extend a second distance from actuation structure proximal end 122, e.g., due to a compression of actuation structure 120. Illustratively, the second distance from actuation structure proximal end 122 may be greater than the first distance from actuation structure proximal end 122.

FIG. 1B illustrates a cross-sectional view of handle 100. In one or more embodiments, handle 100 may comprise fixation mechanism housing 140, an optic fiber sleeve housing 145, an inner bore 150, an inner bore proximal taper 155, and a piston tube guide 160. Handle 100 may be manufactured from any suitable material, e.g., polymers, metals, metal alloys, etc., or from any combination of suitable materials.

FIGS. 2A, 2B, and 2C are schematic diagrams illustrating a housing tube 200. In one or more embodiments, housing tube 200 may comprise a housing tube distal end 201 and a housing tube proximal end 202. Housing tube 200 may be manufactured from any suitable material, e.g., polymers, metals, metal alloys, etc., or from any combination of suitable materials. FIG. 2A illustrates a housing tube 200 oriented to illustrate a first housing tube portion 220. Illustratively, first housing tube portion 220 may have a first stiffness. FIG. 2B illustrates a housing tube 200 oriented to illustrate a second housing tube portion 230. Illustratively, second housing tube portion 230 may have a second stiffness. In one or more embodiments, the second stiffness may be greater than the first stiffness. Illustratively, first housing tube portion 220 may comprise a first material having a first stiffness. In one or more embodiments, second housing tube portion 230 may comprise a second material having a second stiffness. Illustratively, the second stiffness may be greater than the first stiffness.

In one or more embodiments, housing tube 200 may comprise a non-uniform inner diameter or a non-uniform outer diameter, e.g., to vary a stiffness of one or more portions of housing tube 200. Illustratively, a first housing tube portion 220 may comprise a first inner diameter of housing tube 200 and a second housing tube portion 230 may comprise a second inner diameter of housing tube 200. In one or more embodiments, the first inner diameter of housing tube 200 may be larger than the second inner diameter of housing tube 200. Illustratively, a first housing tube portion 220 may comprise a first outer diameter of housing tube 200 and a second housing tube portion 230 may comprise a second outer diameter of housing tube 200. In one or more embodiments, the first outer diameter of housing tube 200 may be smaller than the second outer diameter of housing tube 200.

In one or more embodiments, first housing tube portion 220 may comprise one or more apertures configured to produce a first stiffness of first housing tube portion 220. Illustratively, second housing tube portion 230 may comprise a solid portion of housing tube 200 having a second stiffness. In one or more embodiments, the second stiffness may be greater than the first stiffness. Illustratively, first housing tube portion 220 may comprise one or more apertures configured to produce a first stiffness of first housing tube portion 220. In one or more embodiments, second housing tube portion 230 may comprise one or more apertures configured to produce a second stiffness of second housing tube portion 230. Illustratively, the second stiffness may be greater than the first stiffness.

In one or more embodiments, first housing tube portion 220 may comprise a plurality of slits configured to separate one or more solid portions of housing tube 200. Illustratively, a plurality of slits may be cut, e.g., laser cut, into first housing tube portion 220. In one or more embodiments, first housing tube portion 220 may comprise a plurality of slits configured to minimize a force of friction between housing tube 200 and a cannula, e.g., as housing tube 200 is inserted into the cannula or as housing tube 200 is extracted from the cannula. For example, each slit of the plurality of slits may comprise one or more arches configured to minimize a force of friction between housing tube 200 and a cannula.

FIG. 2C illustrates an angled view of housing tube 200. Illustratively, an optic fiber 250 may be disposed within housing tube 200. In one or more embodiments, optic fiber 250 may be disposed within housing tube 200 wherein an optic fiber distal end 251 is adjacent to housing tube distal end 201. Illustratively, optic fiber 250 may be disposed within housing tube 200 wherein optic fiber 250 may be adjacent to a portion of first housing tube portion 220. In one or more embodiments, a portion of optic fiber 250 may be fixed to an inner portion of housing tube 200, e.g., by a biocompatible adhesive or by any suitable fixation means.

Figure 3:
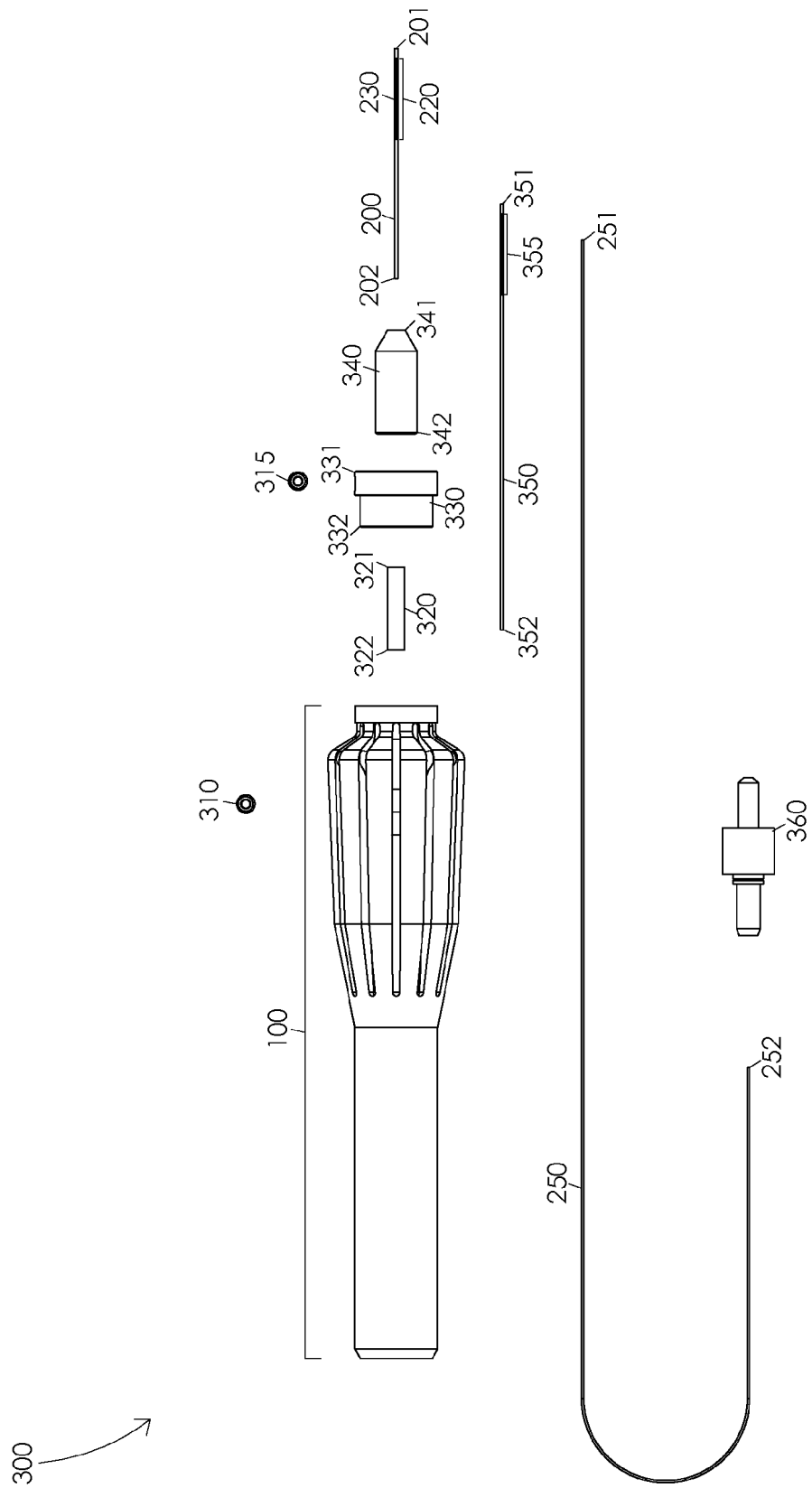
FIG. 3 is a schematic diagram illustrating an exploded view of a steerable laser probe assembly.

FIG. 3 is a schematic diagram illustrating an exploded view of a steerable laser probe assembly 300. In one or more embodiments, steerable laser probe assembly 300 may comprise a handle 100, a housing tube 200 having a housing tube distal end 201 and a housing tube proximal end 202, an optic fiber 250 having an optic fiber distal end 251 and an optic fiber proximal end 252, a fixation mechanism 310, a nosecone fixation mechanism 315, a piston tube 320 having a piston tube distal end 321 and a piston tube proximal end 322, an outer nosecone 330 having an outer nosecone distal end 331 and an outer nosecone proximal end 332, an inner nosecone 340 having an inner nosecone distal end 341 and an inner nosecone proximal end 342, an optic fiber sleeve 350 having an optic fiber sleeve distal end 351 and an optic fiber sleeve proximal end 352, and a light source interface 360. Illustratively, light source interface 360 may be configured to interface with optic fiber 250, e.g., at optic fiber proximal end 252. In one or more embodiments, light source interface 360 may comprise a standard light source connecter, e.g., an SMA connector.

Illustratively, housing tube 200 may be fixed to inner nosecone 340, e.g., housing tube proximal end 202 may be fixed to inner nosecone distal end 341. In one or more embodiments, housing tube 200 may be fixed to inner nosecone 340, e.g., by an adhesive or by any suitable fixation means. Illustratively, a portion of housing tube 200 may be disposed within inner nosecone 340, e.g., housing tube proximal end 202 may be disposed within inner nosecone 340. In one or more embodiments, a portion of housing tube 200 may be fixed within inner nosecone 340, e.g., by an adhesive or by any suitable fixation means. Illustratively, inner nosecone 340 and housing tube 200 may be manufactured as a single unit Inner nosecone 340 may be manufactured from any suitable material, e.g., polymers, metals, metal alloys, etc., or from any combination of suitable materials.

Illustratively, inner nosecone 340 may be fixed to outer nosecone 330, e.g., inner nosecone proximal end 342 may be fixed to outer nosecone distal end 331. In one or more embodiments, inner nosecone 340 may be fixed to outer nosecone 330, e.g., by an adhesive or by any suitable fixation means. Illustratively, a portion or inner nosecone 340 may be disposed within outer nosecone 330, e.g., inner nosecone proximal end 342 may be disposed within outer nosecone 330. In one or more embodiments, a portion of inner nosecone 340 may be fixed within outer nosecone 330, e.g., by an adhesive or by any suitable fixation means. Illustratively, nosecone fixation mechanism 315 may be configured to fix inner nosecone 340 within outer nosecone 330. In one or more embodiments, nosecone fixation mechanism 315 may comprise a set screw configured to firmly attach inner nosecone 340 and outer nosecone 330. Illustratively, nosecone fixation mechanism 315 may be configured to fix inner nosecone 340 within outer nosecone 330, e.g., by a press fit or by any suitable fixation means. For example, nosecone fixation mechanism 315 may be disposed within both outer nosecone 330 and inner nosecone 340, e.g., to firmly fix inner nosecone 340 within outer nosecone 330. Illustratively, inner nosecone 340 and outer nosecone 330 may be manufactured as a single unit. Outer nosecone 330 may be manufactured from any suitable material, e.g., polymers, metals, metal alloys, etc., or from any combination of suitable materials.

In one or more embodiments, piston tube 320 may be fixed to outer nosecone 330, e.g., piston tube distal end 321 may be fixed to outer nosecone proximal end 332. Illustratively, piston tube 320 may be fixed to outer nosecone 330, e.g., by an adhesive or by any suitable fixation means. In one or more embodiments, a portion of piston tube 320 may be disposed within outer nosecone 330, e.g., piston tube distal end 321 may be discs posed within outer nosecone 330. Illustratively, a portion of piston tube 320 may be fixed within outer nosecone 330, e.g., by an adhesive or by any suitable fixation means. In one or more embodiments, piston tube 320 and outer nosecone 330 may be manufactured as a single unit. Illustratively, outer nosecone 330, piston tube 320, and inner nosecone 340 may be manufactured as a single unit. Piston tube 320 may be manufactured from any suitable material, e.g., polymers, metals, metal alloys, etc., or from any combination of suitable materials.

In one or more embodiments, outer nosecone 330 may be fixed to handle distal end 101, e.g., by an adhesive or by any suitable fixation means. Illustratively, outer nosecone 330 may be fixed to actuation ring 130, e.g., by an adhesive or any suitable fixation means. In one or more embodiments, piston tube 320 may be partially or completely disposed within handle 100, e.g., piston tube 320 may be partially or completely disposed within actuation structure 120. Illustratively, a portion of piston tube 320 may be disposed within piston tube guide 160. For example, piston tube proximal end 322 may be disposed within piston tube guide 160. Illustratively, a portion of outer nosecone 330 may be disposed within handle 100, e.g., outer nosecone proximal end 332 may be disposed within handle 100. In one or more embodiments, a portion of outer nosecone 330 may be disposed within actuation structure 120, e.g., outer nosecone proximal end 332 may be disposed within actuation structure 120. Illustratively, a portion of outer nosecone 330 may be disposed within actuation ring 130, e.g., outer nosecone proximal end 332 may be disposed within actuation ring 130. In one or more embodiments, a portion of outer nosecone 330 may be fixed within actuation ring 130, e.g., by an adhesive or by any suitable fixation means.

In one or more embodiments, optic fiber 250 may be disposed within optic fiber sleeve 350. Illustratively, optic fiber sleeve 350 may be configured to protect a portion of optic fiber 250. In one or more embodiments, optic fiber sleeve 350 may be configured to increase a stiffness of a portion of optic fiber 250. Illustratively, optic fiber sleeve 350 may be configured to dissipate a force applied to optic fiber sleeve 350, e.g., to prevent the applied force from damaging optic fiber 250. In one or more embodiments, optic fiber sleeve 350 may comprise an optic fiber sleeve flexible portion 355. Illustratively, optic fiber sleeve flexible portion 355 may comprise one or more apertures in optic fiber sleeve 350. In one or more embodiments, optic fiber sleeve flexible portion 355 may comprise a flexible material. Illustratively, optic fiber sleeve 350 may comprise a non-uniform inner diameter or a non-uniform outer diameter, e.g., to vary a stiffness of one or more portions of optic fiber sleeve 350. In one or more embodiments, optic fiber sleeve flexible portion 355 may comprise a portion of optic fiber sleeve 350 having a reduced outer diameter or an increased inner diameter. Optic fiber sleeve 350 may be manufactured from any suitable material, e.g., polymers, metals, metal alloys, etc., or from any combination of suitable materials.

Illustratively, optic fiber sleeve 350 may be disposed within optic fiber sleeve housing 145, piston tube guide 160, piston tube 320, outer nosecone 330, inner nosecone 340, and housing tube 200. In one or more embodiments, optic fiber sleeve 350 may be disposed within housing tube 200 wherein optic fiber sleeve flexible portion 355 is adjacent to first housing tube portion 220. Illustratively, a portion of optic fiber sleeve 350 may be fixed to an inner portion of housing tube 200, e.g., optic fiber sleeve distal end 351 may be fixed to an inner portion of housing tube 200. In one or more embodiments, a portion of optic fiber sleeve 350 may be fixed within housing tube 200, e.g., by an adhesive or by any suitable fixation means. Illustratively, fixation mechanism 310 may be disposed within fixation mechanism housing 140. In one or more embodiments, fixation mechanism 310 may be configured to fix optic fiber sleeve 350 in a position relative to handle base 110. Illustratively, a portion of fixation mechanism 310 may be disposed in optic fiber sleeve housing 145. In one or more embodiments, fixation mechanism 310 may comprise a set screw configured to fix optic fiber sleeve 350 in a position relative to handle base 110, e.g., by a press fit or by any suitable fixation means. Illustratively, a portion of optic fiber sleeve 350 may be fixed to fixation mechanism 310, e.g., by an adhesive or by any other suitable fixation means.

In one or more embodiments, optic fiber 250 may be disposed within inner bore 150, optic fiber sleeve 350, optic fiber sleeve housing 145, piston tube guide 160, piston tube 320, outer nosecone 330, inner nosecone 340, and housing tube 200. Illustratively, optic fiber 250 may be disposed within housing tube 200 wherein optic fiber distal end 251 may be adjacent to housing tube distal end 201. In one or more embodiments, optic fiber 250 may be disposed within optic fiber sleeve 350 wherein optic fiber distal end 251 extends from optic fiber sleeve distal end 351. Illustratively, a portion of optic fiber 250 may be fixed to an inner portion of housing tube 200, e.g., optic fiber distal end 251 may be fixed to an inner portion of housing tube 200. In one or more embodiments, a portion of optic fiber 250 may be fixed within housing tube 200, e.g., by an adhesive or by any suitable fixation means.

Illustratively, a compression of actuation structure 120 may be configured to actuate actuation ring 130, piston tube 320, outer nosecone 330, inner nose cone 340, and housing tube 200 relative to handle base 110. In one or more embodiments, a compression of actuation structure 120 may be configured to extend actuation ring 130, piston tube 320, outer nosecone 330, inner nosecone 340, and housing tube 200 relative to handle base 110. Illustratively, an extension of housing tube 200 relative to handle base 110 may be configured to cause optic fiber sleeve 350 to apply a force to a portion of housing tube 200, e.g., first housing tube portion 220. For example, since optic fiber sleeve 350 may be fixed in a position relative to handle base 110, e.g., by fixation mechanism 310, and since optic fiber sleeve 350 may also fixed to an inner portion of housing tube 200, an extension of housing tube 200 relative to handle base 110 may be configured to apply a compressive force to a portion of housing tube 200. In one or more embodiments, an application of a force to housing tube 200 may be configured to compress a portion of housing tube 200, e.g., first housing tube portion 220. Illustratively, a compression of a portion of housing tube 200 may be configured to cause housing tube 200 to gradually curve. In one or more embodiments, a gradual curving of housing tube 200 may be configured to gradually curve optic fiber sleeve 350. Illustratively, a gradual curving of optic fiber sleeve 350 may be configured to gradually curve optic fiber 250. In one or more embodiments, a compression of actuation structure 120 may be configured to gradually curve optic fiber 250.

Illustratively, a decompression of actuation structure 120 may be configured to actuate actuation ring 130, piston tube 320, outer nosecone 330, inner nose cone 340, and housing tube 200 relative to handle base 110. In one or more embodiments, a decompression of actuation structure 120 may be configured to retract actuation ring 130, piston tube 320, outer nosecone 330, inner nosecone 340, and housing tube 200 relative to handle base 110. Illustratively, a retraction of housing tube 200 relative to handle base 110 may be configured to cause optic fiber sleeve 350 to reduce a force applied to a portion of housing tube 200, e.g., first housing tube portion 220. For example, since optic fiber sleeve 350 may be fixed in a position relative to handle base 110, e.g., by fixation mechanism 310, and since optic fiber sleeve 350 may also fixed to an inner portion of housing tube 200, a refraction of housing tube 200 relative to handle base 110 may be configured to reduce a compressive force applied to a portion of housing tube 200. In one or more embodiments, a reduction of a force applied to housing tube 200 may be configured to decompress a portion of housing tube 200, e.g., first housing tube portion 220. Illustratively, a decompression of a portion of housing tube 200 may be configured to cause housing tube 200 to gradually straighten. In one or more embodiments, a gradual straightening of housing tube 200 may be configured to gradually straighten optic fiber sleeve 350. Illustratively, a gradual straightening of optic fiber sleeve 350 may be configured to gradually straighten optic fiber 250. In one or more embodiments, a decompression of actuation structure 120 may be configured to gradually straighten optic fiber 250.

Figure 4A:
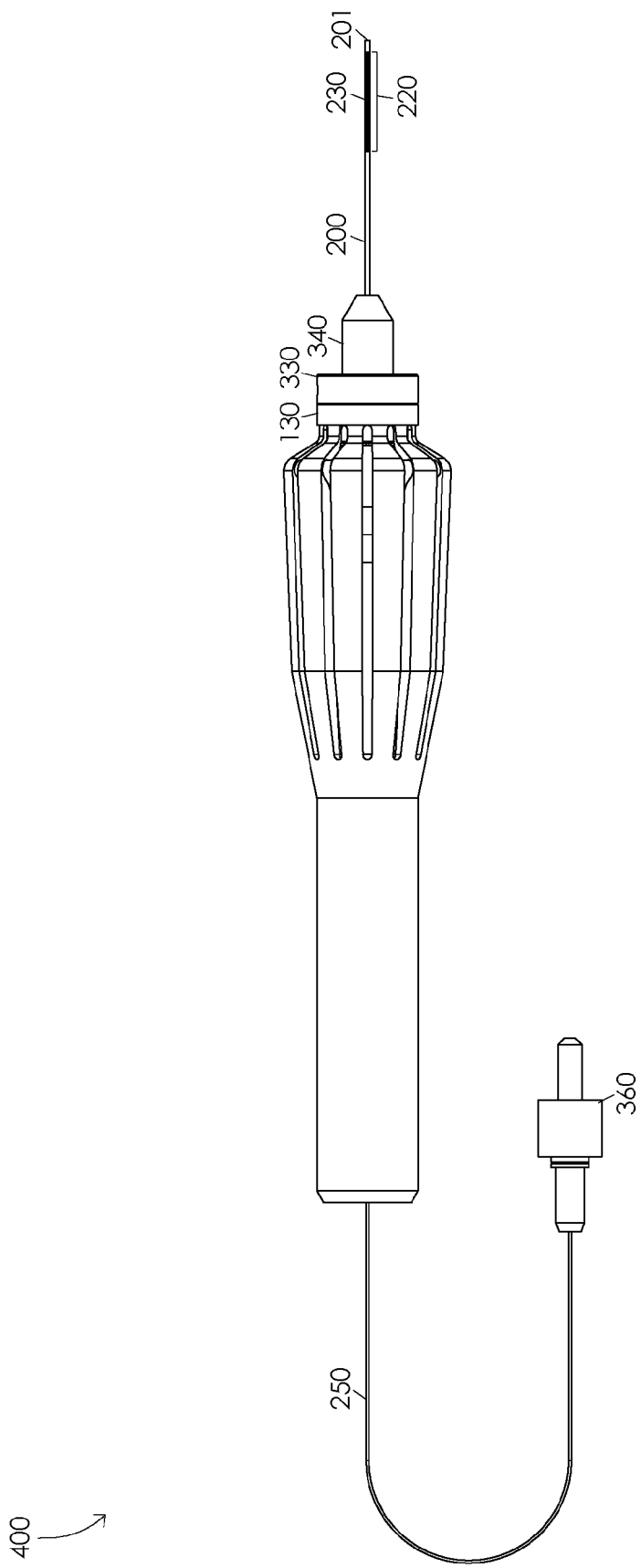
FIGS. 4A, 4B, 4C, 4D, and 4E illustrate a gradual curving of an optic fiber.

FIGS. 4A, 4B, 4C, 4D, and 4E illustrate a gradual curving of an optic fiber 250. FIG. 4A illustrates a straight optic fiber 400. In one or more embodiments, optic fiber 250 may comprise a straight optic fiber 400, e.g., when actuation ring 130 is fully retracted relative to handle base 110. Illustratively, optic fiber 250 may comprise a straight optic fiber 400, e.g., when housing tube 200 is fully retracted relative to handle base 110. In one or more embodiments, optic fiber 250 may comprise a straight optic fiber 400, e.g., when first housing tube portion 220 is fully decompressed. Illustratively, optic fiber 250 may comprise a straight optic fiber 400, e.g., when actuation structure 120 is fully decompressed. In one or more embodiments, a line tangent to optic fiber distal end 251 may be parallel to a line tangent to housing tube proximal end 202, e.g., when optic fiber 250 comprises a straight optic fiber 400.

Figure 4B:
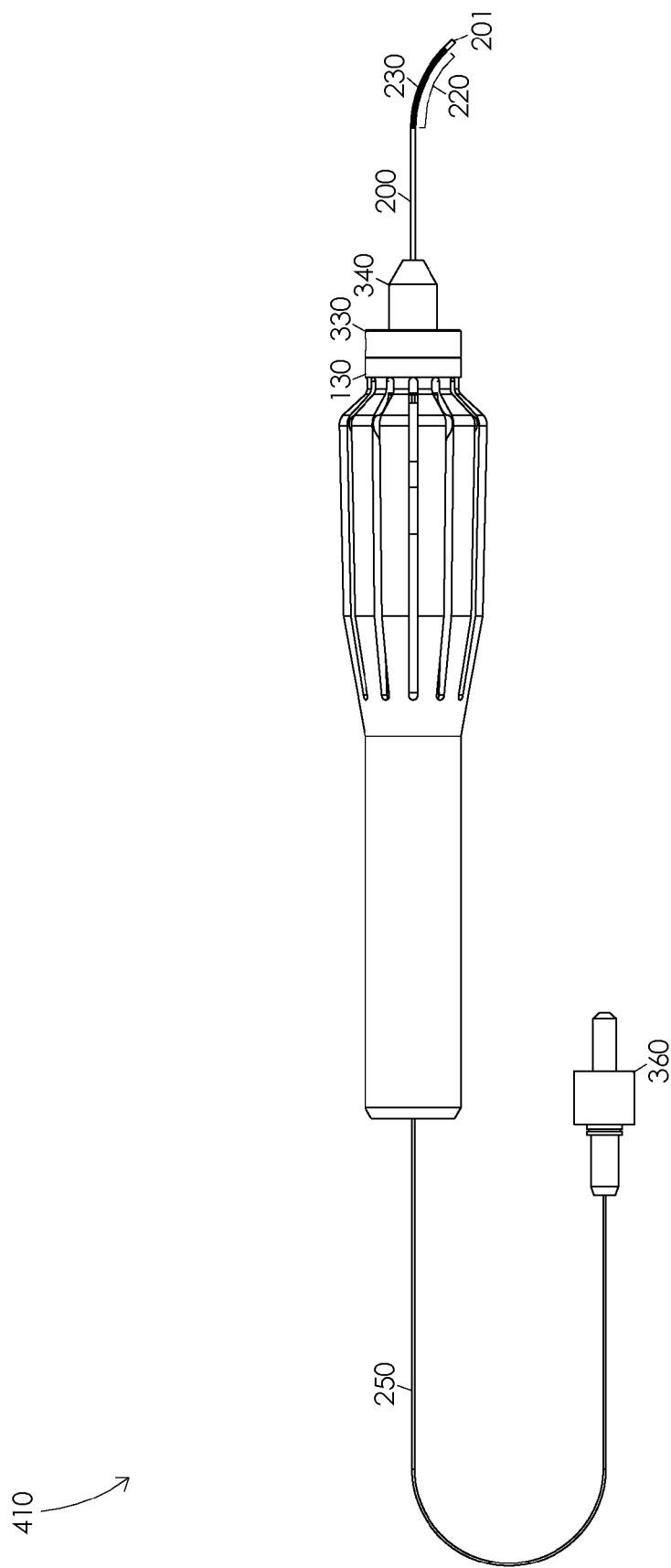

FIG. 4B illustrates an optic fiber in a first curved position 410. In one or more embodiments, a compression of actuation structure 120 may be configured to gradually curve optic fiber 250 from a straight optic fiber 400 to an optic fiber in a first curved position 410. Illustratively, a compression of actuation structure 120 may be configured to gradually extend housing tube 200 relative to optic fiber sleeve 350. In one or more embodiments, a gradual extension of housing tube 200 relative to optic fiber sleeve 350 may be configured to cause optic fiber sleeve 350 to apply a compressive force to a portion of housing tube 200, e.g., a first housing tube portion 220. Illustratively, an application of a compressive force to a portion of housing tube 200, e.g., a first housing tube portion 220, may be configured to cause housing tube 200 to gradually curve. In one or more embodiments, a gradual curving of housing tube 200 may be configured to gradually curve optic fiber 250, e.g., from a straight optic fiber 400 to an optic fiber in a first curved position 410. Illustratively, a line tangent to optic fiber distal end 251 may intersect a line tangent to housing tube proximal end 202 at a first angle, e.g., when optic fiber 250 comprises an optic fiber in a first curved position 410. In one or more embodiments, the first angle may comprise any angle greater than zero degrees. For example, the first angle may comprise a 45 degree angle.

Figure 4C:
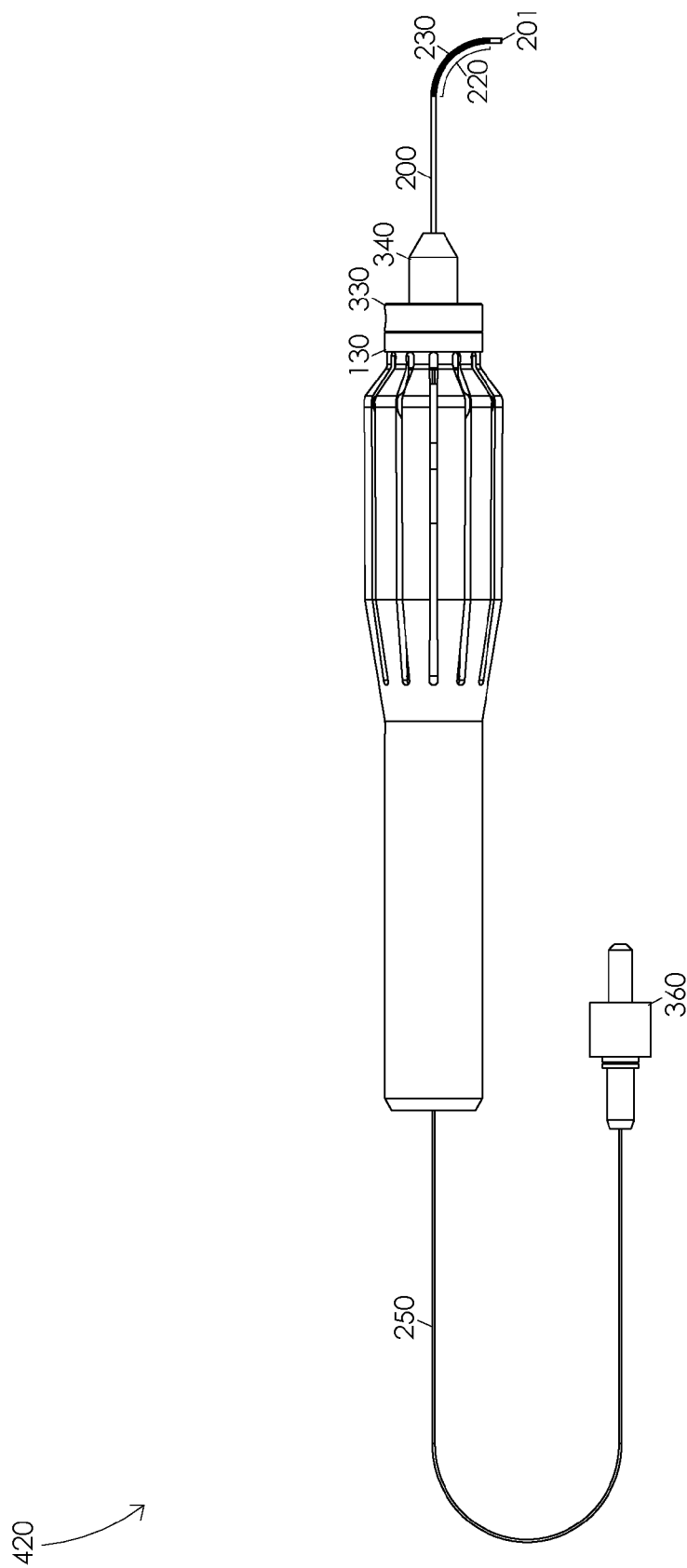

FIG. 4C illustrates an optic fiber in a second curved position 420. In one or more embodiments, a compression of actuation structure 120 may be configured to gradually curve optic fiber 250 from an optic fiber in a first curved position 410 to an optic fiber in a second curved position 420. Illustratively, a compression of actuation structure 120 may be configured to gradually extend housing tube 200 relative to optic fiber sleeve 350. In one or more embodiments, a gradual extension of housing tube 200 relative to optic fiber sleeve 350 may be configured to cause optic fiber sleeve 350 to apply a compressive force to a portion of housing tube 200, e.g., a first housing tube portion 220. Illustratively, an application of a compressive force to a portion of housing tube 200, e.g., a first housing tube portion 220, may be configured to cause housing tube 200 to gradually curve. In one or more embodiments, a gradual curving of housing tube 200 may be configured to gradually curve optic fiber 250, e.g., from an optic fiber in a first curved position 410 to an optic fiber in a second curved position 420. Illustratively, a line tangent to optic fiber distal end 251 may intersect a line tangent to housing tube proximal end 202 at a second angle, e.g., when optic fiber 250 comprises an optic fiber in a second curved position 420. In one or more embodiments, the second angle may comprise any angle greater than the first angle. For example, the second angle may comprise a 90 degree angle.

Figure 4D:
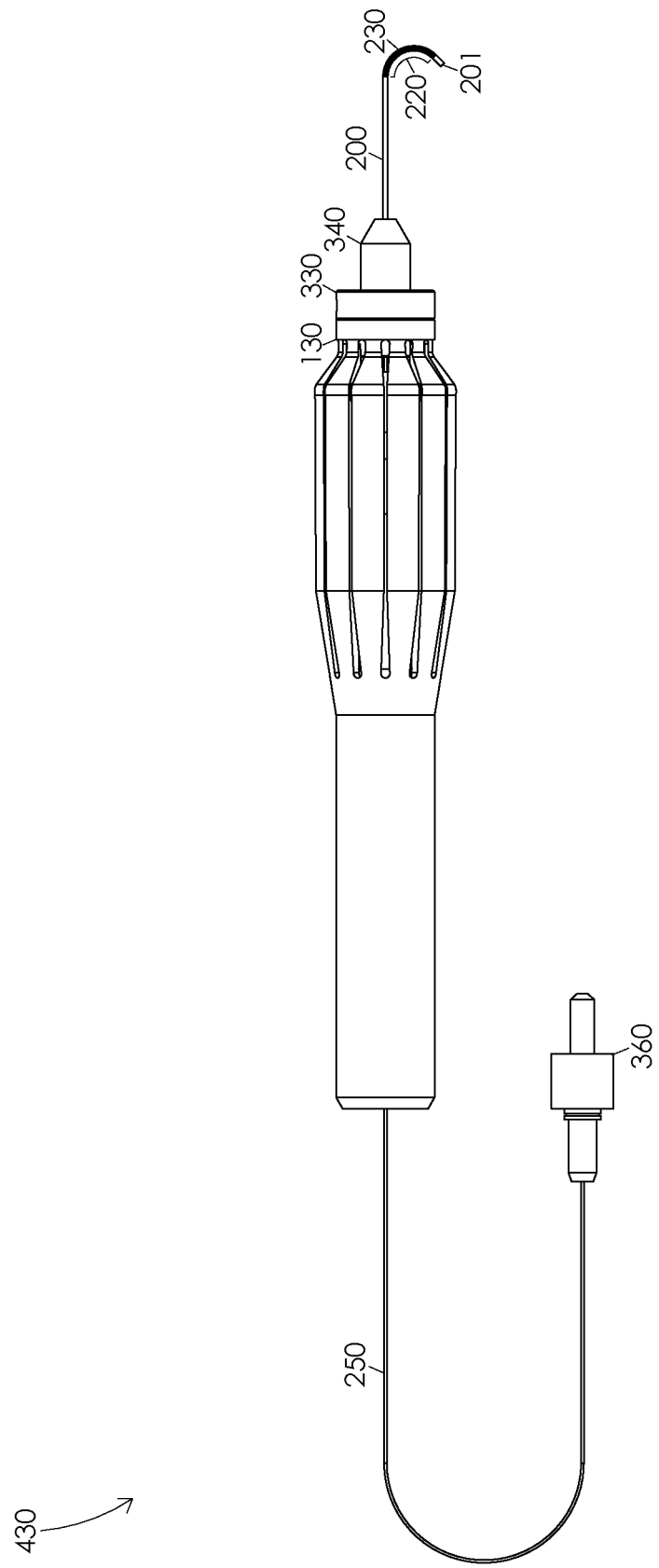

FIG. 4D illustrates an optic fiber in a third curved position 430. In one or more embodiments, a compression of actuation structure 120 may be configured to gradually curve optic fiber 250 from an optic fiber in a second curved position 420 to an optic fiber in a third curved position 430. Illustratively, a compression of actuation structure 120 may be configured to gradually extend housing tube 200 relative to optic fiber sleeve 350. In one or more embodiments, a gradual extension of housing tube 200 relative to optic fiber sleeve 350 may be configured to cause optic fiber sleeve 350 to apply a compressive force to a portion of housing tube 200, e.g., a first housing tube portion 220. Illustratively, an application of a compressive force to a portion of housing tube 200, e.g., a first housing tube portion 220, may be configured to cause housing tube 200 to gradually curve. In one or more embodiments, a gradual curving of housing tube 200 may be configured to gradually curve optic fiber 250, e.g., from an optic fiber in a second curved position 420 to an optic fiber in a third curved position 430. Illustratively, a line tangent to optic fiber distal end 251 may intersect a line tangent to housing tube proximal end 202 at a third angle, e.g., when optic fiber 250 comprises an optic fiber in a third curved position 430. In one or more embodiments, the third angle may comprise any angle greater than the second angle. For example, the third angle may comprise a 135 degree angle.

Figure 4E:
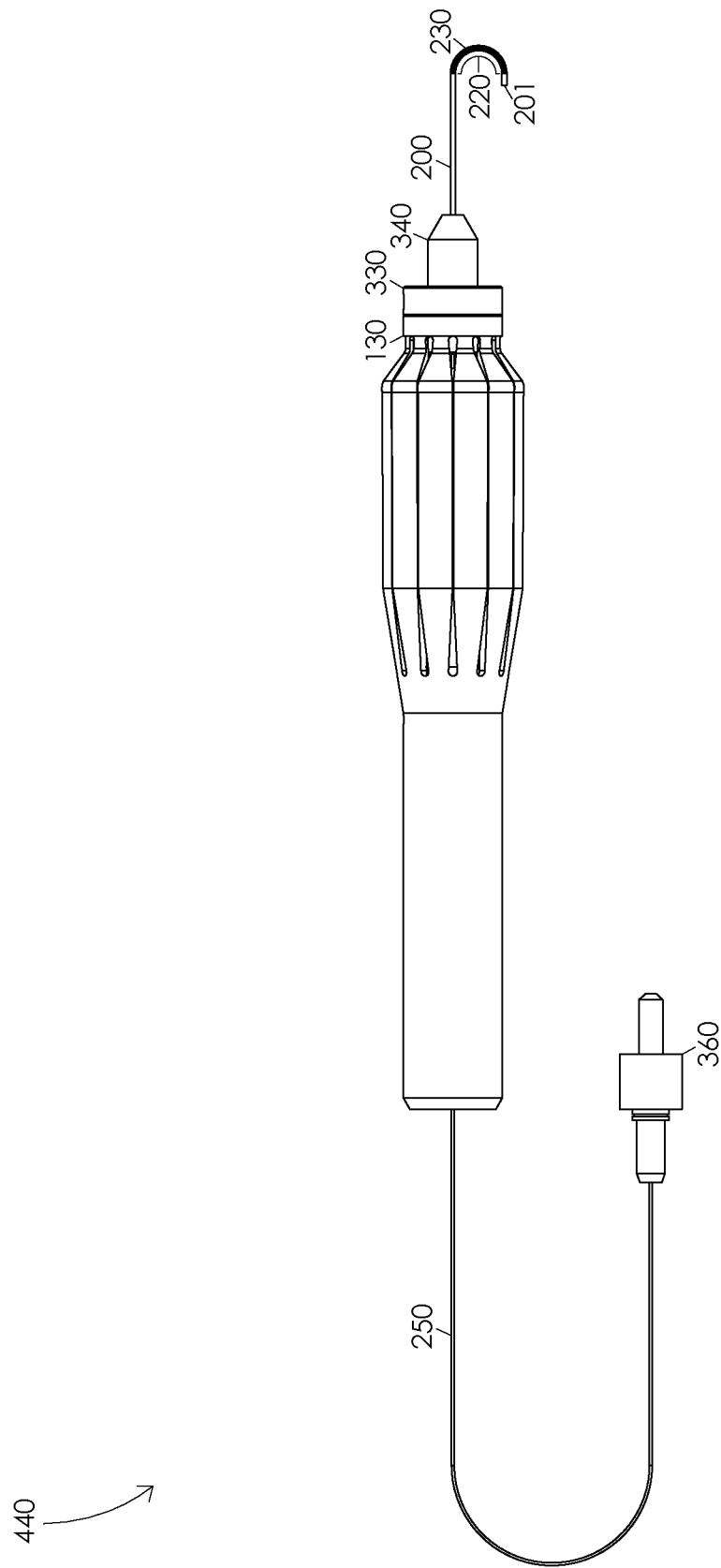

FIG. 4E illustrates an optic fiber in a fourth curved position 440. In one or more embodiments, a compression of actuation structure 120 may be configured to gradually curve optic fiber 250 from an optic fiber in a third curved position 430 to an optic fiber in a fourth curved position 440. Illustratively, a compression of actuation structure 120 may be configured to gradually extend housing tube 200 relative to optic fiber sleeve 350. In one or more embodiments, a gradual extension of housing tube 200 relative to optic fiber sleeve 350 may be configured to cause optic fiber sleeve 350 to apply a compressive force to a portion of housing tube 200, e.g., a first housing tube portion 220. Illustratively, an application of a compressive force to a portion of housing tube 200, e.g., a first housing tube portion 220, may be configured to cause housing tube 200 to gradually curve. In one or more embodiments, a gradual curving of housing tube 200 may be configured to gradually curve optic fiber 250, e.g., from an optic fiber in a third curved position 430 to an optic fiber in a fourth curved position 440. Illustratively, a line tangent to optic fiber distal end 251 may be parallel to a line tangent to housing tube proximal end 202, e.g., when optic fiber 250 comprises an optic fiber in a fourth curved position 440.

In one or more embodiments, one or more properties of a steerable laser probe may be adjusted to attain one or more desired steerable laser probe features. For example, a length that housing tube 200 extends from inner nosecone 340 may be adjusted to vary an amount of compression of actuation structure 120 configured to curve housing tube 200 to a particular curved position. Illustratively, a length of optic fiber sleeve 350 may be adjusted to vary an amount of compression of actuation structure 120 configured to curve housing tube 200 to a particular curved position. In one or more embodiments, a stiffness of optic fiber sleeve flexible portion 355 may be adjusted to vary an amount of compression of actuation structure 120 configured to curve housing tube 200 to a particular curved position. Illustratively, a location or a geometry of optic fiber sleeve flexible portion 355 may be adjusted to vary an amount of compression of actuation structure 120 configured to curve housing tube 200 to a particular curved position. In one or more embodiments, a stiffness of first housing tube portion 220 or a stiffness of second housing tube portion 230 may be adjusted to vary an amount of compression of actuation structure 120 configured to curve housing tube 200 to a particular curved position. Illustratively, a material comprising first housing tube portion 220 or a material comprising second housing tube portion 230 may be adjusted to vary an amount of compression of actuation structure 120 configured to curve housing tube 200 to a particular curved position.

In one or more embodiments, a number of apertures in housing tube 200 may be adjusted to vary an amount of compression of actuation structure 120 configured to curve housing tube 200 to a particular curved position. Illustratively, a location of one or more apertures in housing tube 200 may be adjusted to vary an amount of compression of actuation structure 120 configured to curve housing tube 200 to a particular curved position. In one or more embodiments, a geometry of one or more apertures in housing tube 200 may be adjusted to vary an amount of compression of action structure 120 configured to curve housing tube 200 to a particular curved position. Illustratively, a geometry of one or more apertures in housing tube 200 may be uniform, e.g., each aperture of the one or more apertures may have a same geometry. In one or more embodiments, a geometry of one or more apertures in housing tube 200 may be non-uniform, e.g., a first aperture in housing tube 200 may have a first geometry and a second aperture in housing tube 200 may have a second geometry.

Illustratively, a distance that inner nosecone distal end 341 extends from handle proximal end 102 may be adjusted to vary an amount of compression of actuation structure 120 configured to curve housing tube 200 to a particular curved position. In one or more embodiments, a geometry of actuation structure 120 may be adjusted to vary an amount of compression of actuation structure 120 configured to curve housing tube 200 to a particular curved position. Illustratively, one or more locations within housing tube 200 wherein optic fiber sleeve 350 may be fixed to an inner portion of housing tube 200 may be adjusted to vary an amount of compression of actuation structure 120 configured to curve housing tube 200 to a particular curved position. In one or more embodiments, optic fiber sleeve 350 may not be included in a steerable laser probe, e.g., a compression of actuation structure 120 may be configured cause optic fiber 250 to apply a force to a portion of housing tube 200 causing housing tube 200 to gradually curve.

Illustratively, a stiffness of first housing tube portion 220 or a stiffness of second housing tube portion 230 may be adjusted to vary a bend radius of housing tube 200. In one or more embodiments, a stiffness of first housing tube portion 220 or a stiffness of second housing tube portion 230 may be adjusted to vary a radius of curvature of housing tube 200, e.g., when housing tube 200 is in a particular curved position. Illustratively, a number of apertures in housing tube 200 may be adjusted to vary a bend radius of housing tube 200. In one or more embodiments, a number of apertures in housing tube 200 may be adjusted to vary a radius of curvature of housing tube 200, e.g., when housing tube 200 is in a particular curved position. Illustratively, a location or a geometry of one or more apertures in housing tube 200 may be adjusted to vary a bend radius of housing tube 200. In one or more embodiments, a location or a geometry of one or more apertures in housing tube 200 may be adjusted to vary a radius of curvature of housing tube 200, e.g., when housing tube 200 is in a particular curved position.

Figure 5A:
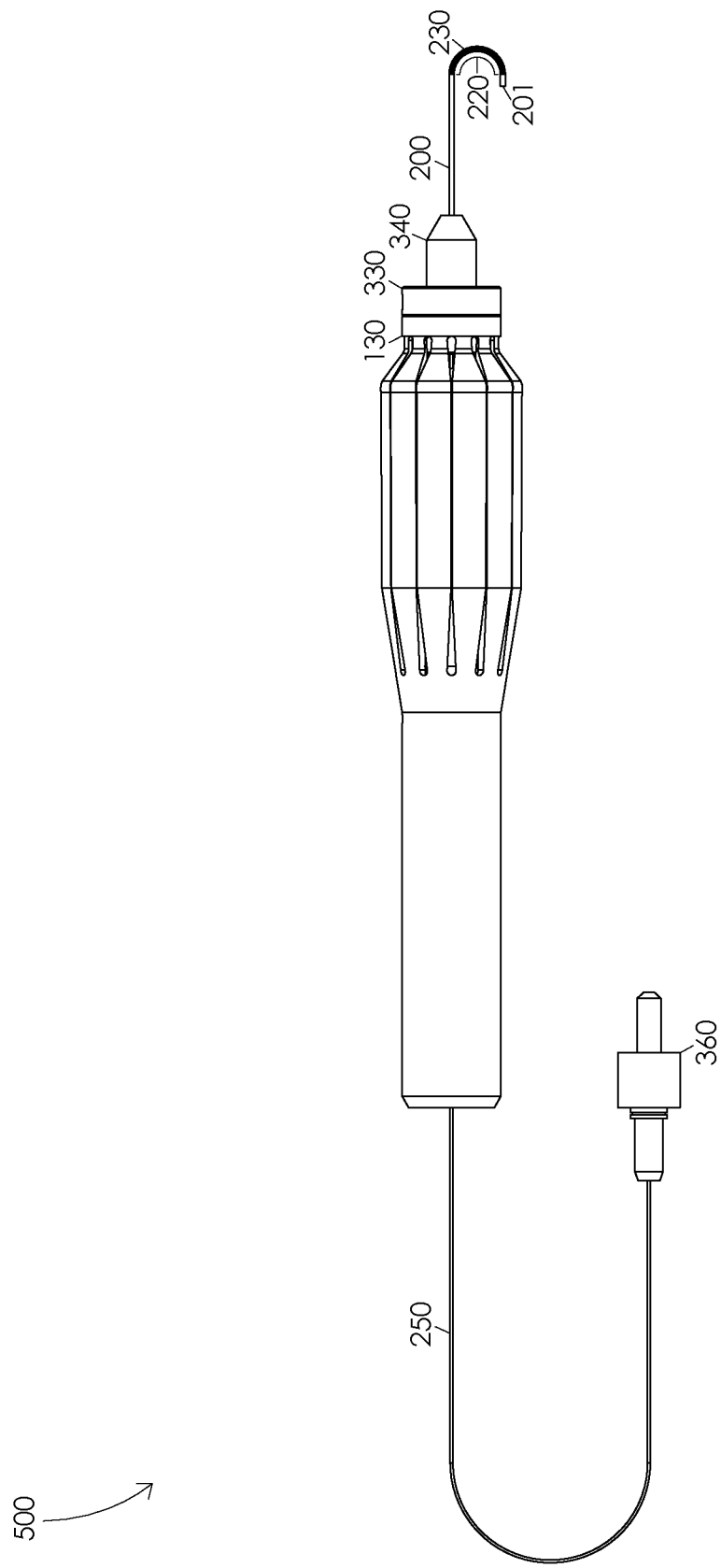
FIGS. 5A, 5B, 5C, 5D, and 5E illustrate a gradual straightening of an optic fiber.

FIGS. 5A, 5B, 5C, 5D, and 5E illustrate a gradual straightening of an optic fiber 250. FIG. 5A illustrates a fully curved optic fiber 500. In one or more embodiments, optic fiber 250 may comprise a fully curved optic fiber 500, e.g., when actuation ring 130 is fully extended relative to handle base 110. Illustratively, optic fiber 250 may comprise a fully curved optic fiber 500, e.g., when housing tube 200 is fully extended relative to optic fiber sleeve 350. In one or more embodiments, optic fiber 250 may comprise a fully curved optic fiber 500, e.g., when first housing tube portion 220 is fully compressed. Illustratively, optic fiber 250 may comprise a fully curved optic fiber 500, e.g., when actuation structure 120 is fully compressed. In one or more embodiments, a line tangent to optic fiber distal end 251 may be parallel to a line tangent to housing tube proximal end 202, e.g., when optic fiber 250 comprises a fully curved optic fiber 500.

Figure 5B:
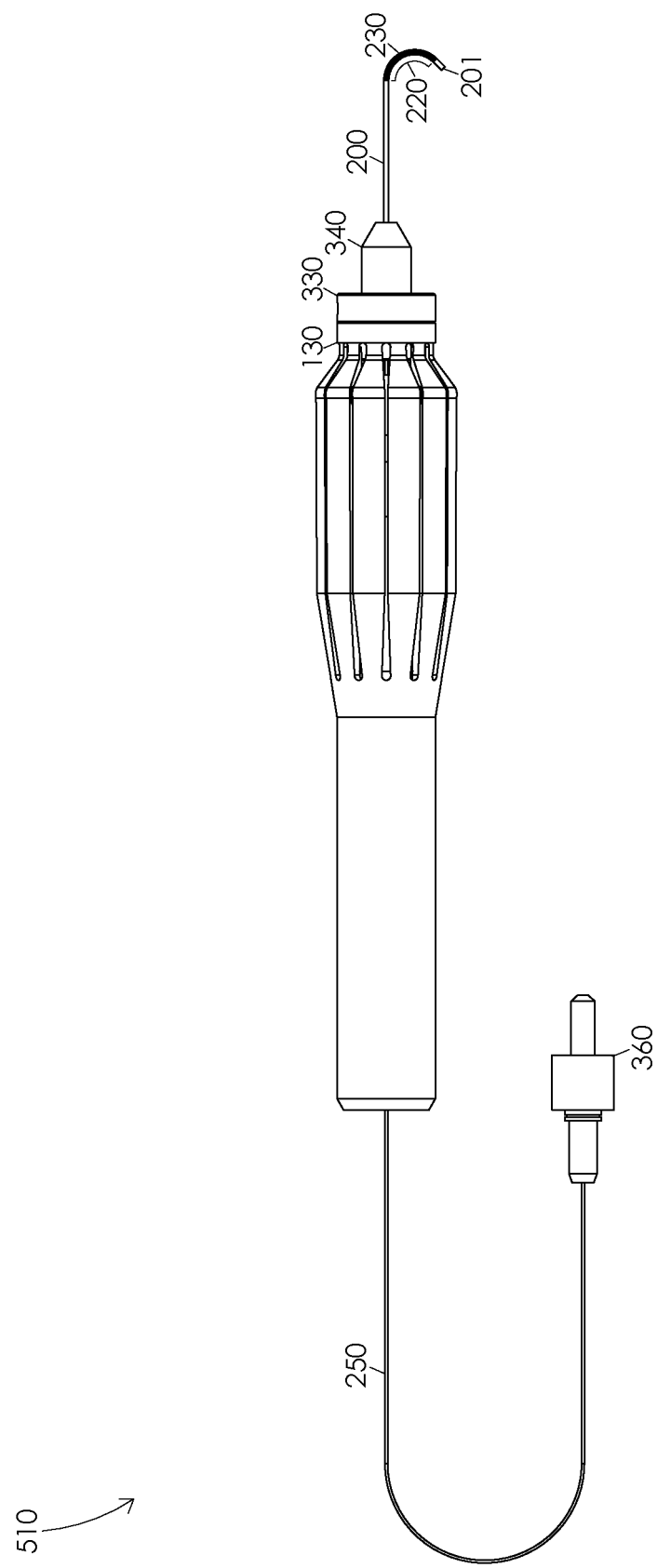

FIG. 5B illustrates an optic fiber in a first partially straightened position 510. In one or more embodiments, a decompression of actuation structure 120 may be configured to gradually straighten optic fiber 250 from a fully curved optic fiber 500 to an optic fiber in a first partially straightened position 510. Illustratively, a decompression of actuation structure 120 may be configured to gradually retract housing tube 200 relative to optic fiber sleeve 350. In one or more embodiments, a gradual retraction of housing tube 200 relative to optic fiber sleeve 350 may be configured to cause optic fiber sleeve 350 to reduce a compressive force applied to a portion of housing tube 200, e.g., a first housing tube portion 220. Illustratively, a reduction of a compressive force applied to a portion of housing tube 200, e.g., a first housing tube portion 220, may be configured to cause housing tube 200 to gradually straighten. In one or more embodiments, a gradual straightening of housing tube 200 may be configured to gradually straighten optic fiber 250, e.g., from a fully curved optic fiber 500 to an optic fiber in a first partially straightened position 510. Illustratively, a line tangent to optic fiber distal end 251 may intersect a line tangent to housing tube proximal end 202 at a first partially straightened angle, e.g., when optic fiber 250 comprises an optic fiber in a first partially straightened position 510. In one or more embodiments, the first partially straightened angle may comprise any angle less than 180 degrees. For example, the first partially straightened angle may comprise a 135 degree angle.

Figure 5C:
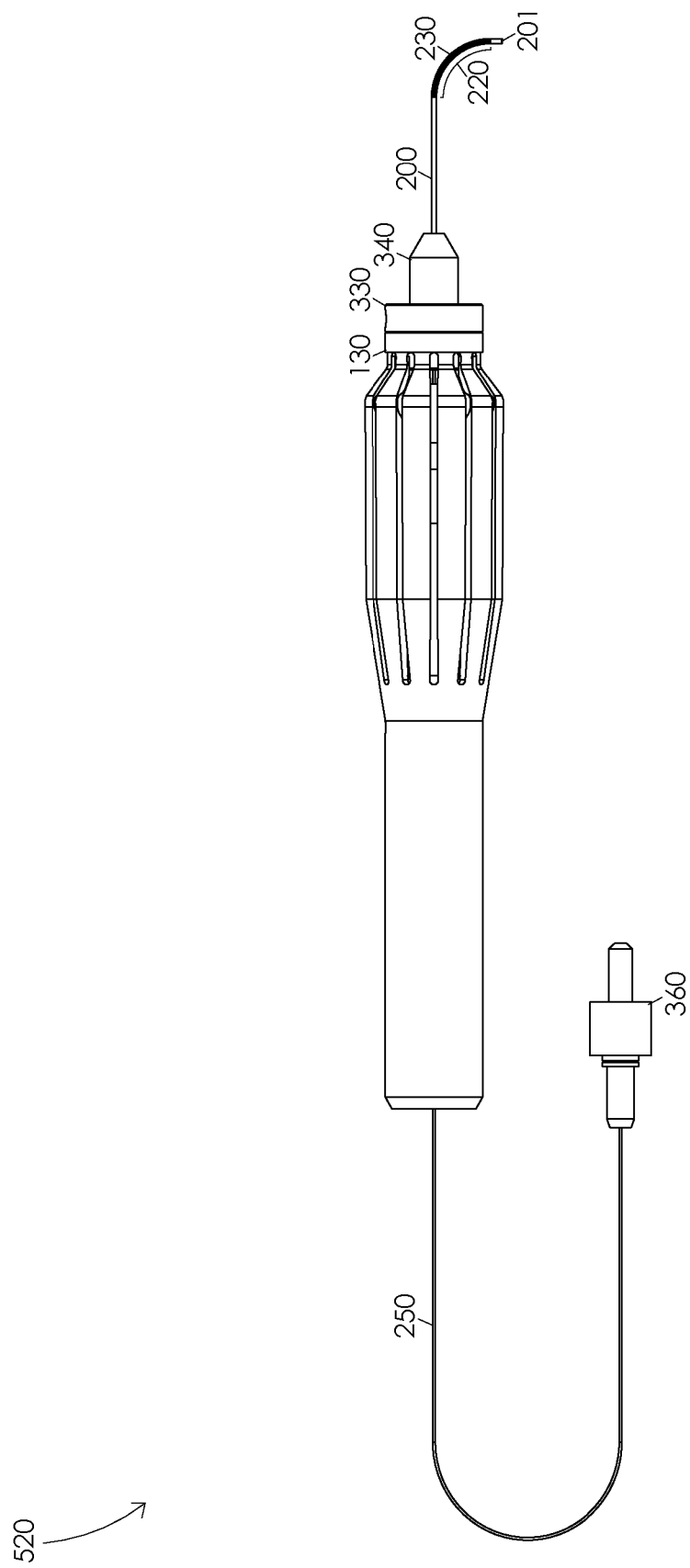

FIG. 5C illustrates an optic fiber in a second partially straightened position 520. In one or more embodiments, a decompression of actuation structure 120 may be configured to gradually straighten optic fiber 250 from an optic fiber in a first partially straightened position 510 to an optic fiber in a second partially straightened position 520. Illustratively, a decompression of actuation structure 120 may be configured to gradually retract housing tube 200 relative to optic fiber sleeve 350. In one or more embodiments, a gradual retraction of housing tube 200 relative to optic fiber sleeve 350 may be configured to cause optic fiber sleeve 350 to reduce a compressive force applied to a portion of housing tube 200, e.g., a first housing tube portion 220. Illustratively, a reduction of a compressive force applied to a portion of housing tube 200, e.g., a first housing tube portion 220, may be configured to cause housing tube 200 to gradually straighten. In one or more embodiments, a gradual straightening of housing tube 200 may be configured to gradually straighten optic fiber 250, e.g., from an optic fiber in a first partially straightened position 510 to an optic fiber in a second partially straightened position 520. Illustratively, a line tangent to optic fiber distal end 251 may intersect a line tangent to housing tube proximal end 202 at a second partially straightened angle, e.g., when optic fiber 250 comprises an optic fiber in a second partially straightened position 520. In one or more embodiments, the second partially straightened angle may comprise any angle less than the first partially straightened angle. For example, the second partially straightened angle may comprise a 90 degree angle.

Figure 5D:
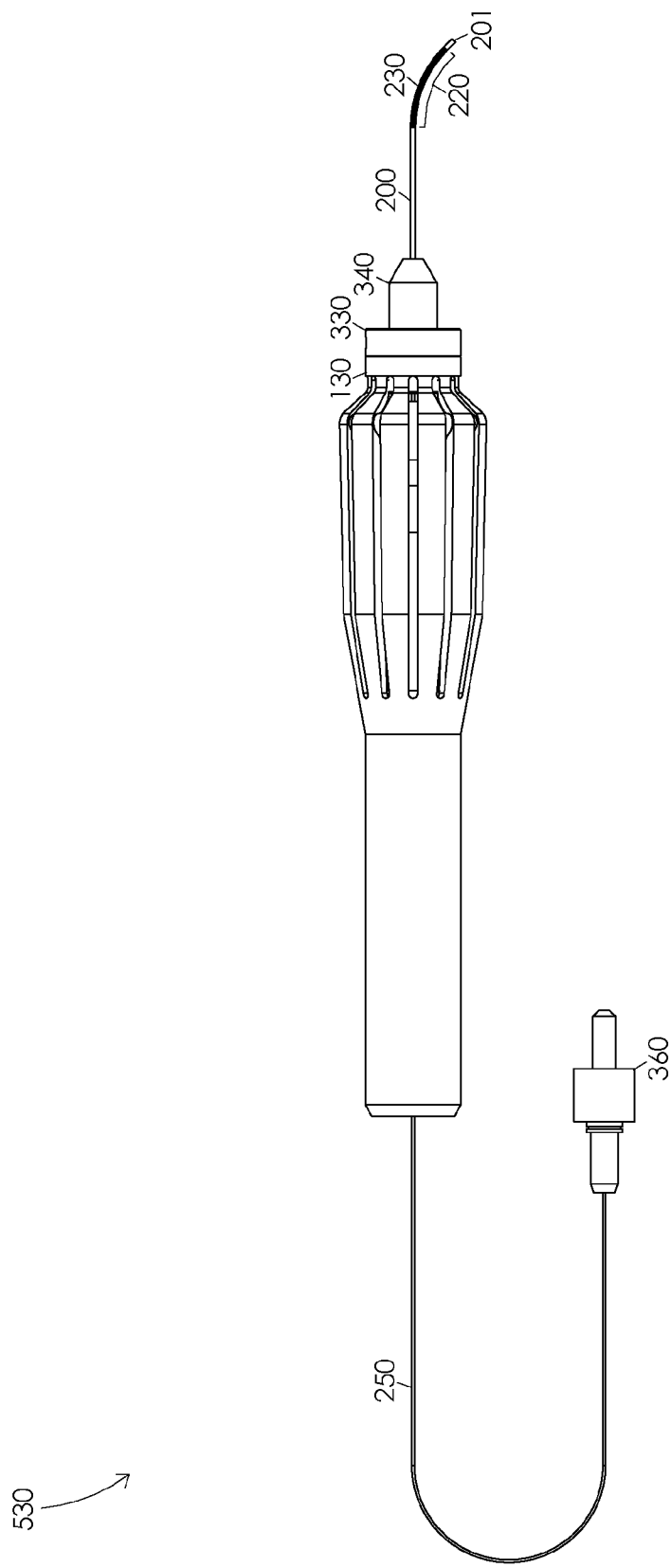

FIG. 5D illustrates an optic fiber in a third partially straightened position 530. In one or more embodiments, a decompression of actuation structure 120 may be configured to gradually straighten optic fiber 250 from an optic fiber in a second partially straightened position 520 to an optic fiber in a third partially straightened position 530. Illustratively, a decompression of actuation structure 120 may be configured to gradually retract housing tube 200 relative to optic fiber sleeve 350. In one or more embodiments, a gradual retraction of housing tube 200 relative to optic fiber sleeve 350 may be configured to cause optic fiber sleeve 350 to reduce a compressive force applied to a portion of housing tube 200, e.g., a first housing tube portion 220. Illustratively, a reduction of a compressive force applied to a portion of housing tube 200, e.g., a first housing tube portion 220, may be configured to cause housing tube 200 to gradually straighten. In one or more embodiments, a gradual straightening of housing tube 200 may be configured to gradually straighten optic fiber 250, e.g., from an optic fiber in a second partially straightened position 520 to an optic fiber in a third partially straightened position 530. Illustratively, a line tangent to optic fiber distal end 251 may intersect a line tangent to housing tube proximal end 202 at a third partially straightened angle, e.g., when optic fiber 250 comprises an optic fiber in a third partially straightened position 530. In one or more embodiments, the third partially straightened angle may comprise any angle less than the second partially straightened angle. For example, the third partially straightened angle may comprise a 45 degree angle.

Figure 5E:
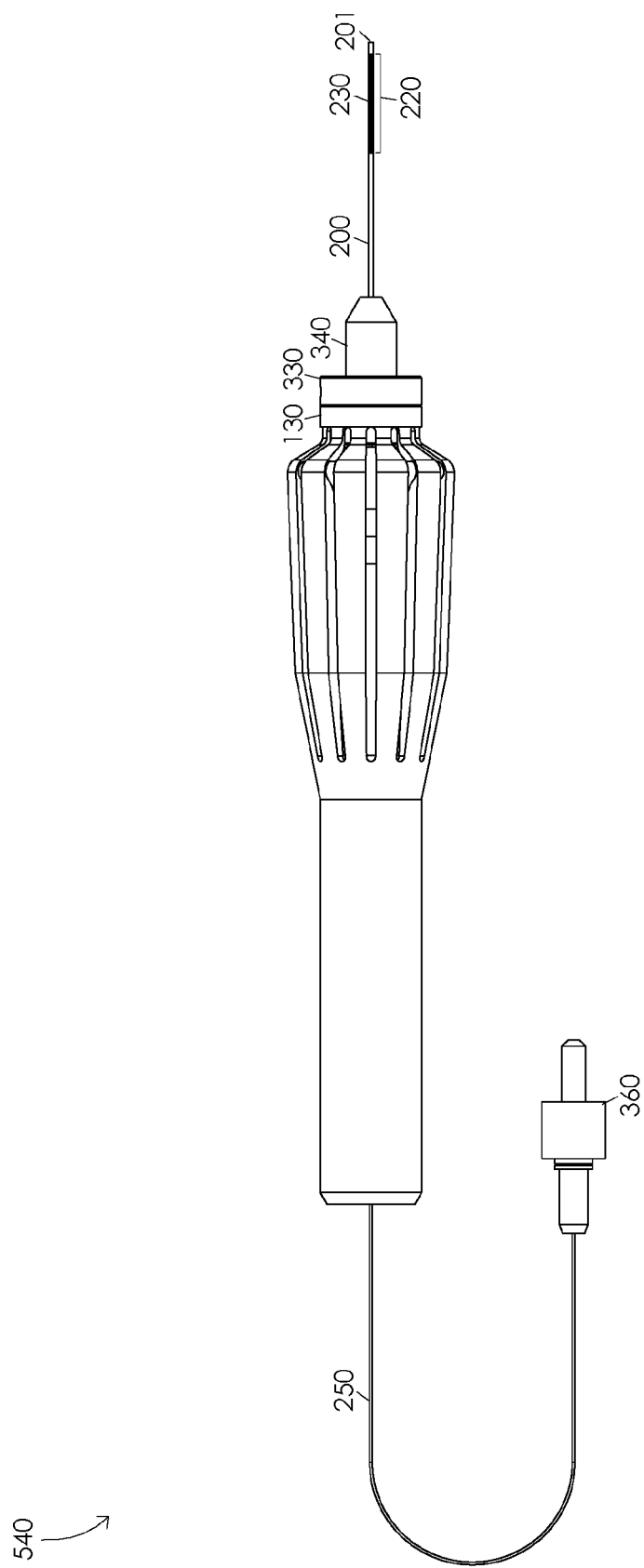

FIG. 5E illustrates an optic fiber in a fully straightened position 540. In one or more embodiments, a decompression of actuation structure 120 may be configured to gradually straighten optic fiber 250 from an optic fiber in a third partially straightened position 530 to an optic fiber in a fully straightened position 540. Illustratively, a decompression of actuation structure 120 may be configured to gradually retract housing tube 200 relative to optic fiber sleeve 350. In one or more embodiments, a gradual retraction of housing tube 200 relative to optic fiber sleeve 350 may be configured to cause optic fiber sleeve 350 to reduce a compressive force applied to a portion of housing tube 200, e.g., a first housing tube portion 220. Illustratively, a reduction of a compressive force applied to a portion of housing tube 200, e.g., a first housing tube portion 220, may be configured to cause housing tube 200 to gradually straighten. In one or more embodiments, a gradual straightening of housing tube 200 may be configured to gradually straighten optic fiber 250, e.g., from an optic fiber in a third partially straightened position 530 to an optic fiber in a fully straightened position 540. Illustratively, a line tangent to optic fiber distal end 251 may be parallel to a line tangent to housing tube proximal end 202, e.g., when optic fiber 250 comprises an optic fiber in a fully straightened position 540.

Illustratively, a surgeon may aim optic fiber distal end 251 at any of a plurality of targets within an eye, e.g., to perform a photocoagulation procedure. In one or more embodiments, a surgeon may aim optic fiber distal end 251 at any target within a particular transverse plane of the inner eye by, e.g., rotating handle 100 to orient housing tube 200 in an orientation configured to cause a curvature of housing tube 200 within the particular transverse plane of the inner eye and varying an amount of compression of actuation structure 120. Illustratively, a surgeon may aim optic fiber distal end 251 at any target within a particular sagittal plane of the inner eye by, e.g., rotating handle 100 to orient housing tube 200 in an orientation configured to cause a curvature of housing tube 200 within the particular sagittal plane of the inner eye and varying an amount of compression of actuation structure 120. In one or more embodiments, a surgeon may aim optic fiber distal end 251 at any target within a particular frontal plane of the inner eye by, e.g., varying an amount of compression of actuation structure 120 to orient a line tangent to optic fiber distal end 251 wherein the line tangent to optic fiber distal end 251 is within the particular frontal plane of the inner eye and rotating handle 100. Illustratively, a surgeon may aim optic fiber distal end 251 at any target located outside of the particular transverse plane, the particular sagittal plane, and the particular frontal plane of the inner eye, e.g., by varying a rotational orientation of handle 100 and varying an amount of compression of actuation structure 120. In one or more embodiments, a surgeon may aim optic fiber distal end 251 at any target of a plurality of targets within an eye, e.g., without increasing a length of a portion of a steerable laser probe within the eye. Illustratively, a surgeon may aim optic fiber distal end 251 at any target of a plurality of targets within an eye, e.g., without decreasing a length of a portion of a steerable laser probe within the eye.

FIGS. 6A and 6B are schematic diagrams illustrating a handle 600. FIG. 6A illustrates a top view of handle 600. In one or more embodiments, handle 600 may comprise a handle distal end 601, a handle proximal end 602, a handle base 610, an actuation structure 620, a housing tube platform 630, and an actuation platform 640. Illustratively, actuation platform 640 may comprise an actuation platform distal end 641 and an actuation platform proximal end 642. In one or more embodiments, actuation structure 620 may comprise a plurality of actuation arms 625. Illustratively, each actuation arm 625 may comprise at least one extension mechanism 626. In one or more embodiments, each actuation arm 625 may comprise an inverted actuation joint 627.

Illustratively, actuation structure 620 may be compressed, e.g., by an application of a compressive force to actuation structure 620. In one or more embodiments, actuation structure 620 may be compressed by an application of one or more compressive forces located at one or more locations around an outer perimeter of actuation structure 620. Illustratively, the one or more locations may comprise any of a plurality of locations around the outer perimeter of actuation structure 620. For example, a surgeon may compress actuation structure 620, e.g., by squeezing actuation structure 620. Illustratively, the surgeon may compress actuation structure 620 by squeezing actuation structure 620 at any particular location of a plurality of locations around an outer perimeter of actuation structure 620. For example, a surgeon may rotate handle 600 and compress actuation structure 620 from any rotational position of a plurality of rotational positions of handle 600.

In one or more embodiments, actuation structure 620 may be compressed by an application of a compressive force to any one or more of the plurality of actuation arms 625. Illustratively, each actuation arm 625 may be configured to actuate independently. In one or more embodiments, each actuation arm 625 may be connected to one or more of the plurality of actuation arms 625 wherein an actuation of a particular actuation arm 625 may be configured to actuate every actuation arm 625 of the plurality of actuation arms 625. In one or more embodiments, a compression of actuation structure 620, e.g., due to an application of a compressive force to a particular actuation arm 625, may be configured to actuate the particular actuation arm 625. Illustratively, an actuation of the particular actuation arm 625 may be configured to actuate every actuation arm 625 of the plurality of actuation arms 625. In one or more embodiments, an application of a compressive force to a particular actuation arm 625 may be configured to extend at least one extension mechanism 626 of the particular actuation arm 625.

Illustratively, an application of a compressive force to a particular actuation arm 625 may be configured to retract actuation platform 640 relative to handle base 610. In one or more embodiments, as a particular actuation arm 625 is compressed, e.g., due to an application of a compressive force to the particular actuation arm 625, an inverted actuation joint 627 of the particular actuation arm 625 may be configured to gradually retract actuation platform 640 relative to handle base 610. Illustratively, inverted actuation joint 627 may be configured to retract actuation platform 640 relative to handle base 610, e.g., by transferring a compressive force applied to actuation structure 620 to a force applied to actuation platform distal end 641. For example, when a compressive force is applied to a particular actuation arm 625, e.g., and the particular actuation arm 625 is extended by at least one extension mechanism 626 of the particular actuation arm 625, an inverted actuation joint 627 of the particular actuation arm 625 may be configured to retract actuation platform 640 relative to handle base 610.

FIG. 6B illustrates a cross-sectional view of handle 600. In one or more embodiments, handle 600 may comprise an inner bore 650, an inner bore proximal taper 651, an actuation mechanism housing 645, an inner bore distal chamber 652, an optic fiber draw sleeve housing 653, and an optic fiber draw sleeve guide 655. Handle 600 may be manufactured from any suitable material, e.g., polymers, metals, metal alloys, etc., or from any combination of suitable materials.

Figure 7C:
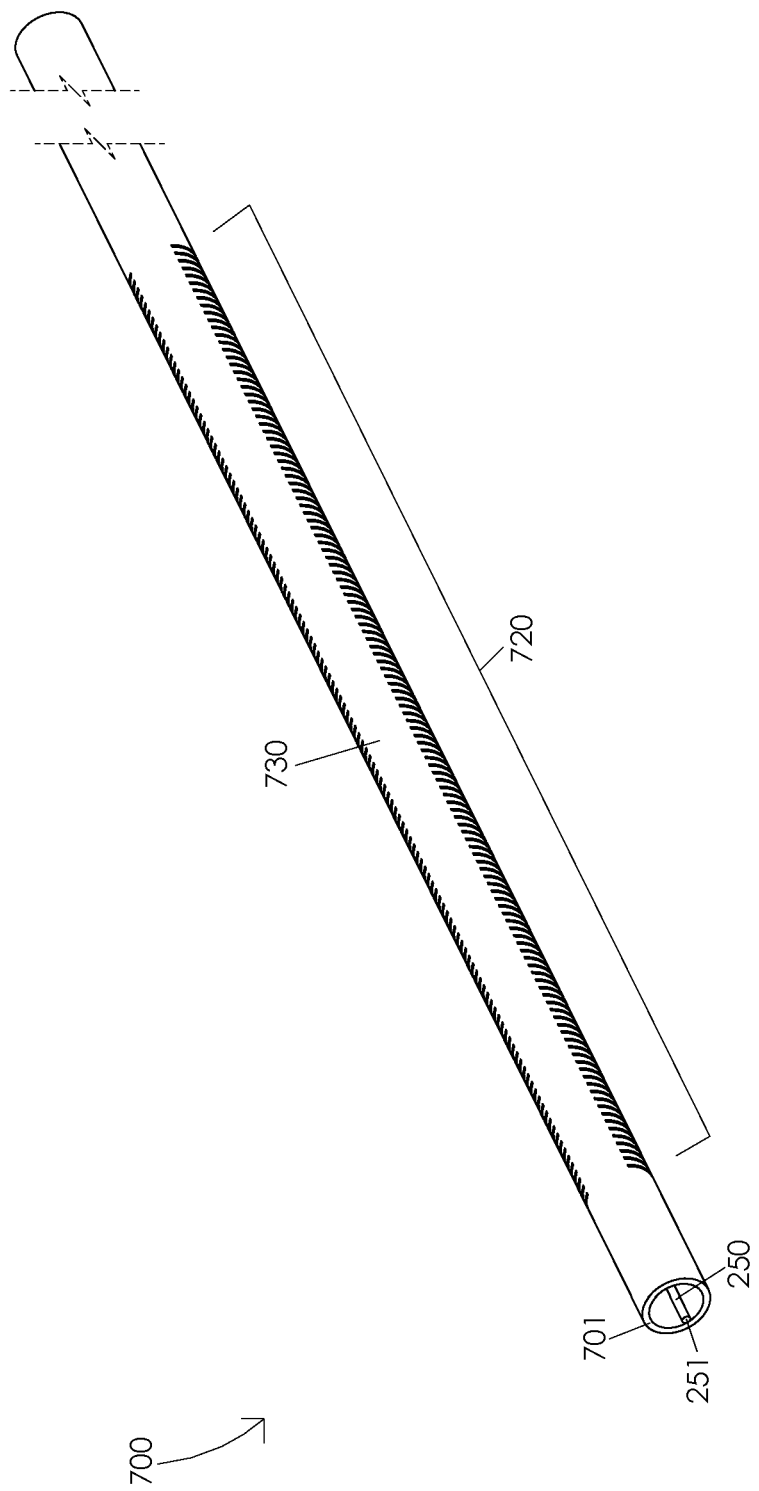

FIGS. 7A, 7B, and 7C are schematic diagrams illustrating a housing tube 700. In one or more embodiments, housing tube 700 may comprise a housing tube distal end 701 and a housing tube proximal end 702. Housing tube 700 may be manufactured from any suitable material, e.g., polymers, metals, metal alloys, etc., or from any combination of suitable materials. FIG. 7A illustrates a housing tube 700 oriented to illustrate a first housing tube portion 720. Illustratively, first housing tube portion 720 may have a first stiffness. FIG. 7B illustrates a housing tube 700 oriented to illustrate a second housing tube portion 730. Illustratively, second housing tube portion 730 may have a second stiffness. In one or more embodiments, the second stiffness may be greater than the first stiffness. Illustratively, first housing tube portion 720 may comprise a first material having a first stiffness. In one or more embodiments, second housing tube portion 730 may comprise a second material having a second stiffness. Illustratively, the second stiffness may be greater than the first stiffness.

In one or more embodiments, housing tube 700 may comprise a non-uniform inner diameter or a non-uniform outer diameter, e.g., to vary a stiffness of one or more portions of housing tube 700. Illustratively, a first housing tube portion 720 may comprise a first inner diameter of housing tube 700 and a second housing tube portion 730 may comprise a second inner diameter of housing tube 700. In one or more embodiments, the first inner diameter of housing tube 700 may be larger than the second inner diameter of housing tube 700. Illustratively, a first housing tube portion 720 may comprise a first outer diameter of housing tube 700 and a second housing tube portion 730 may comprise a second outer diameter of housing tube 700. In one or more embodiments, the first outer diameter of housing tube 700 may be smaller than the second outer diameter of housing tube 700.

In one or more embodiments, first housing tube portion 720 may comprise one or more apertures configured to produce a first stiffness of first housing tube portion 720. Illustratively, second housing tube portion 730 may comprise a solid portion of housing tube 700 having a second stiffness. In one or more embodiments, the second stiffness may be greater than the first stiffness. Illustratively, first housing tube portion 720 may comprise one or more apertures configured to produce a first stiffness of first housing tube portion 720. In one or more embodiments, second housing tube portion 730 may comprise one or more apertures configured to produce a second stiffness of second housing tube portion 730. Illustratively, the second stiffness may be greater than the first stiffness.

In one or more embodiments, first housing tube portion 720 may comprise a plurality of slits configured to separate one or more solid portions of housing tube 700. Illustratively, a plurality of slits may be cut, e.g., laser cut, into first housing tube portion 720. In one or more embodiments, first housing tube portion 720 may comprise a plurality of slits configured to minimize a force of friction between housing tube 700 and a cannula, e.g., as housing tube 700 is inserted into the cannula or as housing tube 700 is extracted from the cannula. For example, each slit of the plurality of slits may comprise one or more arches configured to minimize a force of friction between housing tube 700 and a cannula.

FIG. 7C illustrates an angled view of housing tube 700. Illustratively, an optic fiber 250 may be disposed within housing tube 700. In one or more embodiments, optic fiber 250 may be disposed within housing tube 700 wherein an optic fiber distal end 251 is adjacent to housing tube distal end 701. Illustratively, optic fiber 250 may be disposed within housing tube 700 wherein optic fiber 250 may be adjacent to a portion of first housing tube portion 720. In one or more embodiments, a portion of optic fiber 250 may be fixed to an inner portion of housing tube 700, e.g., by a biocompatible adhesive or by any suitable fixation means.

Figure 8:
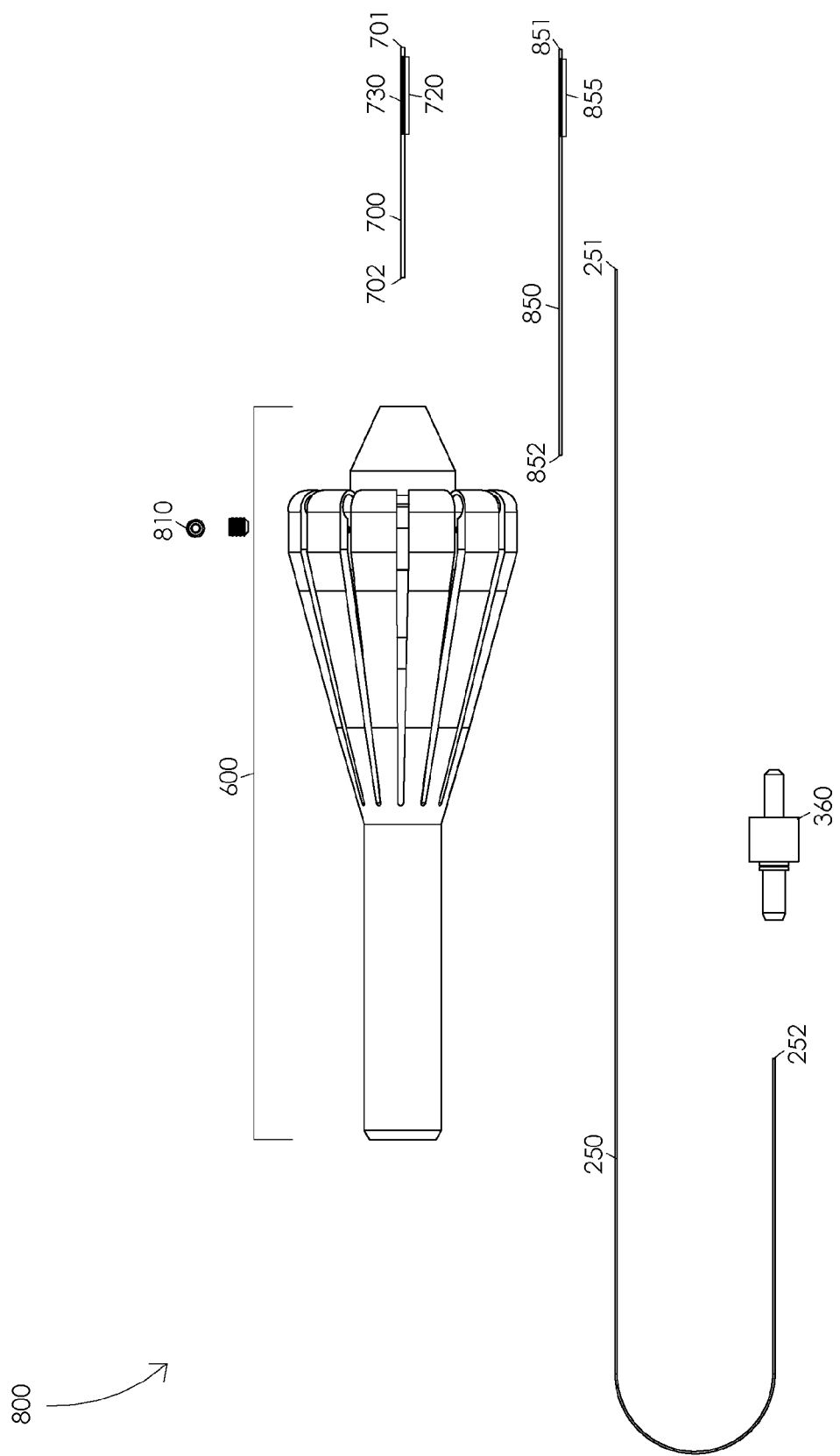
FIG. 8 is a schematic diagram illustrating an exploded view of a steerable laser probe assembly.

FIG. 8 is a schematic diagram illustrating an exploded view of a steerable laser probe assembly 800. In one or more embodiments, steerable laser probe assembly 800 may comprise a handle 600; an actuation mechanism 810; a housing tube 700 having a housing tube distal end 701, a housing tube proximal end 702, a first housing tube portion 720, and a second housing tube portion 730; an optic fiber draw sleeve 850 having an optic fiber draw sleeve distal end 851, an optic fiber draw sleeve proximal end 852, and an optic fiber draw sleeve flexible portion 855; an optic fiber 250 having an optic fiber distal end 251 and an optic fiber proximal end 252; and a light source interface 360. Illustratively, light source interface 360 may be configured to interface with optic fiber 250, e.g., at optic fiber proximal end 252. In one or more embodiments, light source interface 360 may comprise a standard light source connecter, e.g., an SMA connector.

Illustratively, a portion of housing tube 700 may be fixed to housing tube platform 630, e.g., housing tube proximal end 702 may be fixed to handle distal end 601. In one or more embodiments, a portion of housing tube 700 may be fixed to housing tube platform 630, e.g., by an adhesive or by any suitable fixation means. Illustratively, a portion of housing tube 700 may be disposed within housing tube platform 630, e.g., housing tube proximal end 702 may be disposed within housing tube platform 630. In one or more embodiments, a portion of housing tube 700 may be fixed to housing tube platform 630, e.g., by an adhesive or by any suitable fixation means. Illustratively, a portion of housing tube 700 may be disposed within optic fiber draw sleeve guide 655, e.g., housing tube proximal end 702 may be disposed within optic fiber draw sleeve guide 655. In one or more embodiments, a portion of housing tube 700 may be fixed within optic fiber draw sleeve guide 655, e.g., by an adhesive or any suitable fixation means.

In one or more embodiments, optic fiber 250 may be disposed within optic fiber draw sleeve 850. Illustratively, optic fiber draw sleeve 850 may be configured to protect a portion of optic fiber 250. In one or more embodiments, optic fiber draw sleeve 850 may be configured to increase a stiffness of a portion of optic fiber 250. Illustratively, optic fiber draw sleeve 850 may be configured to dissipate a force applied to optic fiber draw sleeve 850, e.g., to prevent the applied force from damaging optic fiber 250. In one or more embodiments, optic fiber draw sleeve 850 may comprise an optic fiber draw sleeve flexible portion 855. Illustratively, optic fiber draw sleeve flexible portion 855 may comprise one or more apertures in optic fiber draw sleeve 850. In one or more embodiments, optic fiber draw sleeve flexible portion 855 may comprise a flexible material. Illustratively, optic fiber draw sleeve 850 may comprise a non-uniform inner diameter or a non-uniform outer diameter, e.g., to vary a stiffness of one or more portions of optic fiber draw sleeve 850. In one or more embodiments, optic fiber draw sleeve flexible portion 855 may comprise a portion of optic fiber draw sleeve 850 having a reduced outer diameter or an increased inner diameter. Optic fiber draw sleeve 850 may be manufactured from any suitable material, e.g., polymers, metals, metal alloys, etc., or from any combination of suitable materials.

Illustratively, optic fiber draw sleeve 850 may be disposed within optic fiber draw sleeve housing 653, actuation mechanism housing 645, optic fiber draw sleeve guide 655, and housing tube 700. In one or more embodiments, optic fiber draw sleeve 850 may be disposed within housing tube 700 wherein optic fiber draw sleeve flexible portion 855 is adjacent to first housing tube portion 720. Illustratively, a portion of optic fiber draw sleeve 850 may be fixed to an inner portion of housing tube 700, e.g., optic fiber draw sleeve distal end 851 may be fixed to an inner portion of housing tube 700. In one or more embodiments, a portion of optic fiber draw sleeve 850 may be fixed within housing tube 700, e.g., by an adhesive or by any suitable fixation means. Illustratively, actuation mechanism 810 may be disposed within actuation mechanism housing 645. In one or more embodiments, actuation mechanism 810 may be configured to fix optic fiber draw sleeve 850 in a position relative to actuation platform 640. Illustratively, a portion of actuation mechanism 810 may be disposed in optic fiber draw sleeve housing 653. In one or more embodiments, actuation mechanism 810 may comprise a set screw configured to fix optic fiber draw sleeve 850 in a position relative to actuation platform 640, e.g., by a press fit or by any suitable fixation means. Illustratively, a portion of optic fiber draw sleeve 850 may be fixed to actuation mechanism 810, e.g., by an adhesive or by any other suitable fixation means.

In one or more embodiments, optic fiber 250 may be disposed within inner bore 650, inner bore distal chamber 652, optic fiber draw sleeve 850, optic fiber draw sleeve housing 653, optic fiber draw sleeve guide 655, and housing tube 700. Illustratively, optic fiber 250 may be disposed within housing tube 700 wherein optic fiber distal end 251 may be adjacent to housing tube distal end 701. In one or more embodiments, optic fiber 250 may be disposed within optic fiber draw sleeve 850 wherein optic fiber distal end 251 extends from optic fiber draw sleeve distal end 851. Illustratively, a portion of optic fiber 250 may be fixed to an inner portion of housing tube 700, e.g., optic fiber distal end 251 may be fixed to an inner portion of housing tube 700. In one or more embodiments, a portion of optic fiber 250 may be fixed within housing tube 700, e.g., by an adhesive or by any suitable fixation means.

Illustratively, a compression of actuation structure 620 may be configured to retract actuation platform 640 relative to handle base 610. In one or more embodiments, a refraction of actuation platform 640 relative to handle base 610 may be configured to retract actuation mechanism 810 relative to handle base 610. Illustratively, a retraction of actuation mechanism 810 relative to handle base 610 may be configured to retract optic fiber draw sleeve 850 relative to handle base 610. Illustratively, a retraction of optic fiber draw sleeve 850 relative to handle base 610 may be configured to retract optic fiber draw sleeve 850 relative to housing tube 700. In one or more embodiments, a compression of actuation structure 620 may be configured to retract optic fiber draw sleeve 850 relative to housing tube 700. Illustratively, a retraction of optic fiber draw sleeve 850 relative to housing tube 700 may be configured to apply a force, e.g., a compressive force, to a portion of housing tube 700, e.g., first housing tube portion 720. In one or more embodiments, an application of a force to a portion of housing tube 700 may be configured to compress a portion of housing tube 700 causing housing tube 700 to gradually curve. Illustratively, a gradual curving of housing tube 700 may be configured to gradually curve optic fiber draw sleeve 850. In one or more embodiments, a gradual curving of optic fiber draw sleeve 850 may be configured to gradually curve optic fiber 250. Illustratively, a gradual curving of housing tube 700, e.g., due to a compression of actuation structure 620, may be configured to gradually curve optic fiber 250.

Illustratively, a decompression of actuation structure 620 may be configured to extend actuation platform 640 relative to handle base 610. In one or more embodiments, an extension of actuation platform 640 relative to handle base 610 may be configured to extend actuation mechanism 810 relative to handle base 610. Illustratively, an extension of actuation mechanism 810 relative to handle base 610 may be configured to extend optic fiber draw sleeve 850 relative to handle base 610. Illustratively, an extension of optic fiber draw sleeve 850 relative to handle base 610 may be configured to extend optic fiber draw sleeve 850 relative to housing tube 700. In one or more embodiments, a decompression of actuation structure 620 may be configured to extend optic fiber draw sleeve 850 relative to housing tube 700. Illustratively, an extension of optic fiber draw sleeve 850 relative to housing tube 700 may be configured to reduce a force, e.g., a compressive force, applied to a portion of housing tube 700, e.g., first housing tube portion 720. In one or more embodiments, a reduction of a force applied to a portion of housing tube 700 may be configured to decompress a portion of housing tube 700 causing housing tube 700 to gradually straighten. Illustratively, a gradual straightening of housing tube 700 may be configured to gradually straighten optic fiber draw sleeve 850. In one or more embodiments, a gradual straightening of optic fiber draw sleeve 850 may be configured to gradually straighten optic fiber 250. Illustratively, a gradual straightening of housing tube 700, e.g., due to a decompression of actuation structure 620, may be configured to gradually straighten optic fiber 250.

Figure 9A:
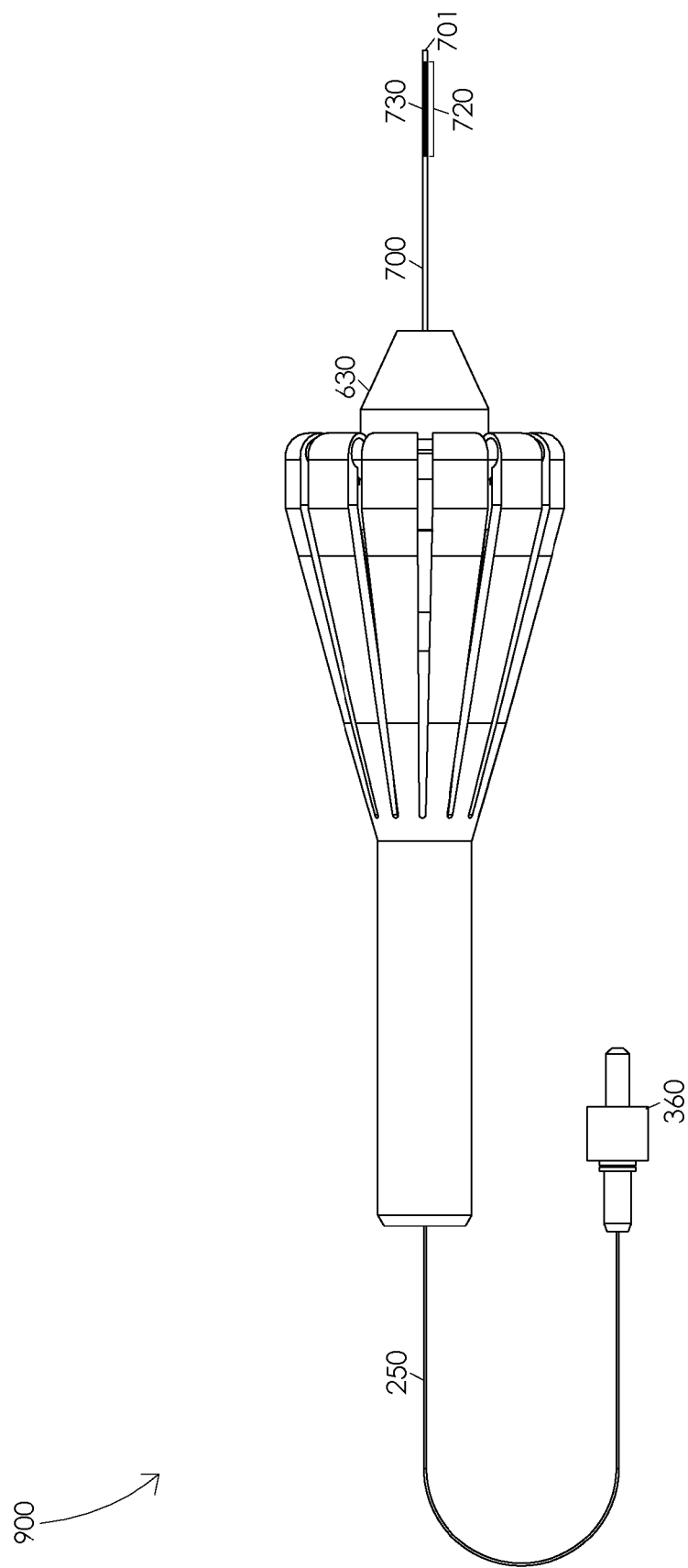
FIGS. 9A, 9B, 9C, 9D, and 9E illustrate a gradual curving of an optic fiber.

FIGS. 9A, 9B, 9C, 9D, and 9E illustrate a gradual curving of an optic fiber 250. FIG. 9A illustrates a straight optic fiber 900. In one or more embodiments, optic fiber 250 may comprise a straight optic fiber 900, e.g., when actuation platform 640 is fully extended relative to handle base 610. Illustratively, optic fiber 250 may comprise a straight optic fiber 900, e.g., when optic fiber draw sleeve 850 is fully extended relative to housing tube 700. In one or more embodiments, optic fiber 250 may comprise a straight optic fiber 900, e.g., when first housing tube portion 720 is fully decompressed. Illustratively, optic fiber 250 may comprise a straight optic fiber 900, e.g., when actuation structure 620 is fully decompressed. In one or more embodiments, a line tangent to optic fiber distal end 251 may be parallel to a line tangent to housing tube proximal end 702, e.g., when optic fiber 250 comprises a straight optic fiber 900.

Figure 9B:
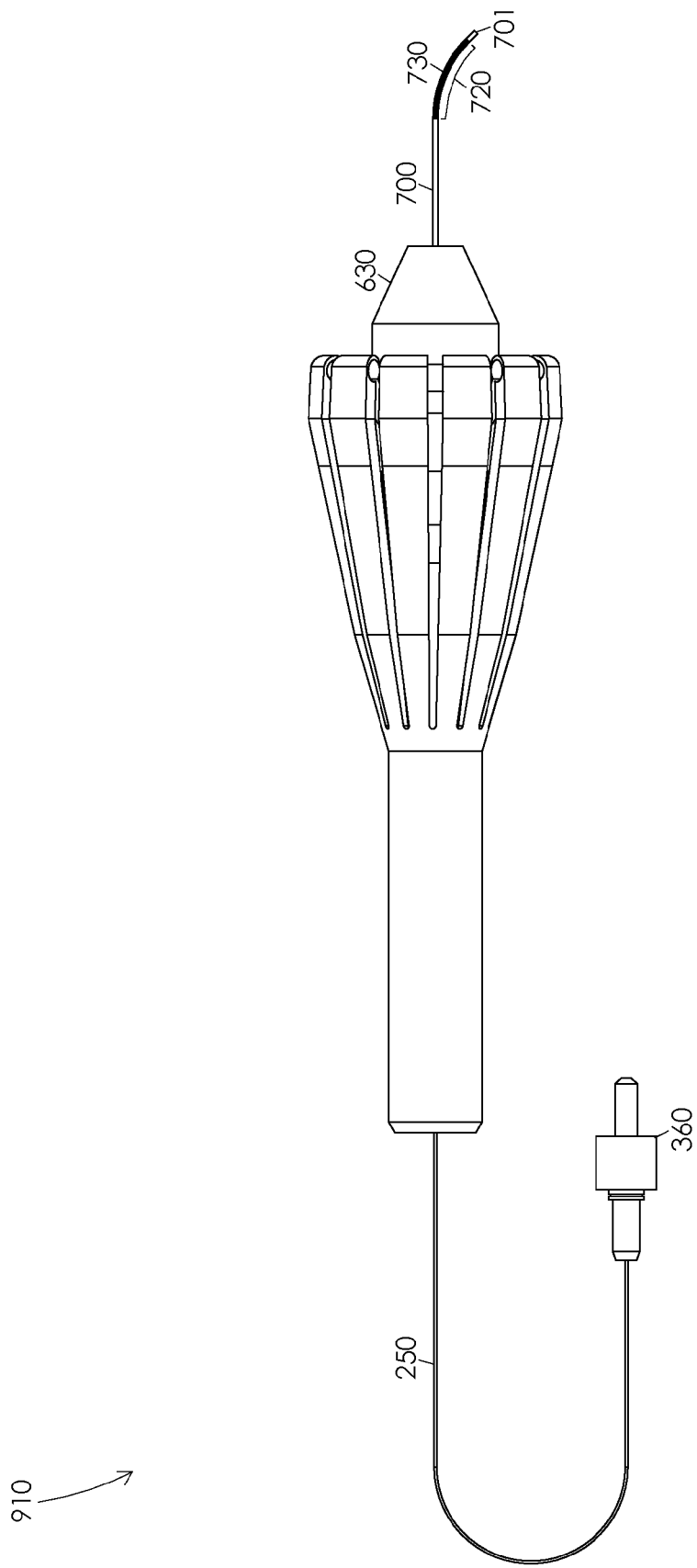

FIG. 9B illustrates an optic fiber in a first curved position 910. In one or more embodiments, a compression of actuation structure 620 may be configured to gradually curve optic fiber 250 from a straight optic fiber 900 to an optic fiber in a first curved position 910. Illustratively, a compression of actuation structure 620 may be configured to gradually retract optic fiber draw sleeve 850 relative to housing tube 700. In one or more embodiments, a gradual retraction of optic fiber draw sleeve 850 relative to housing tube 700 may be configured to cause optic fiber draw sleeve 850 to apply a compressive force to a portion of housing tube 700, e.g., a first housing tube portion 720. Illustratively, an application of a compressive force to a portion of housing tube 700, e.g., a first housing tube portion 720, may be configured to cause housing tube 700 to gradually curve. In one or more embodiments, a gradual curving of housing tube 700 may be configured to gradually curve optic fiber 250, e.g., from a straight optic fiber 900 to an optic fiber in a first curved position 910. Illustratively, a line tangent to optic fiber distal end 251 may intersect a line tangent to housing tube proximal end 702 at a first angle, e.g., when optic fiber 250 comprises an optic fiber in a first curved position 910. In one or more embodiments, the first angle may comprise any angle greater than zero degrees. For example, the first angle may comprise a 45 degree angle.

Figure 9C:
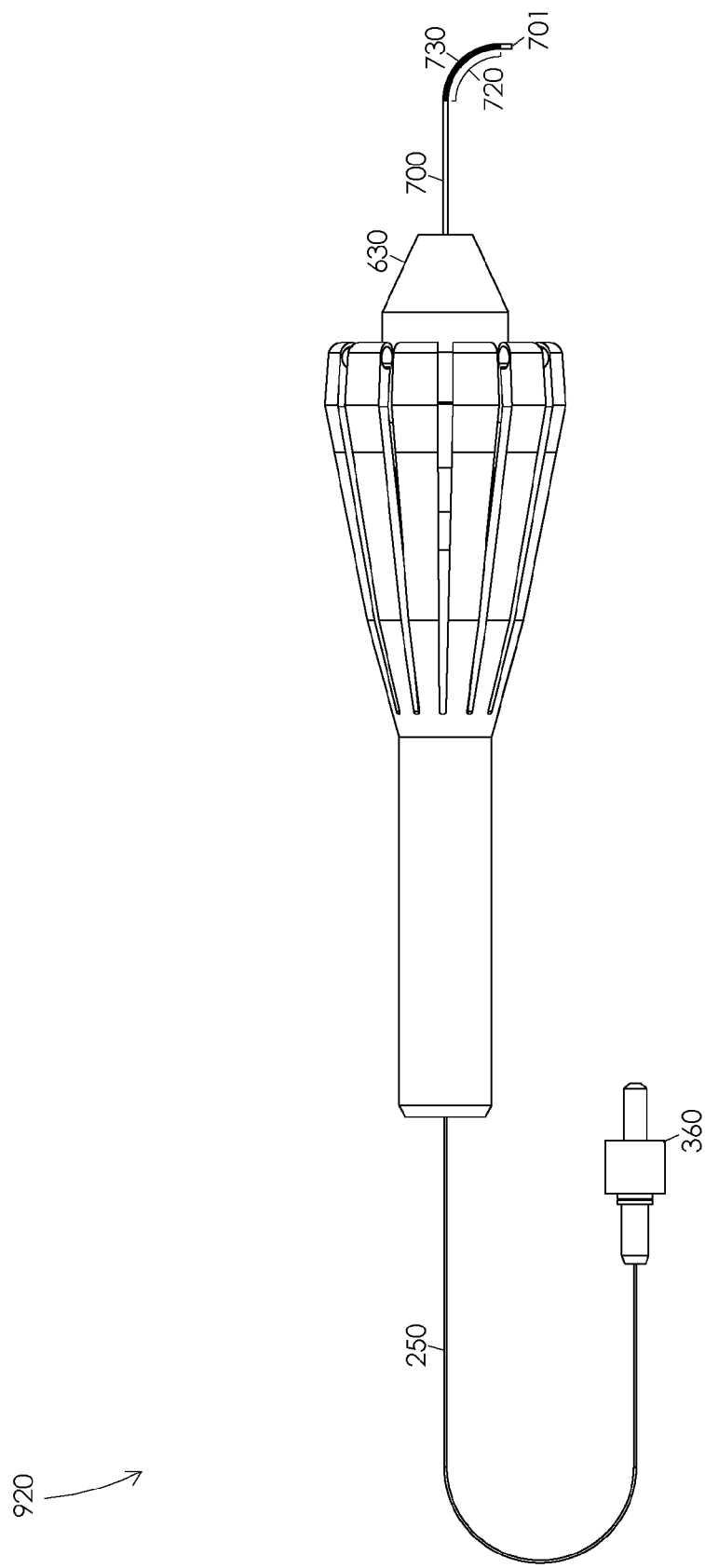

FIG. 9C illustrates an optic fiber in a second curved position 920. In one or more embodiments, a compression of actuation structure 620 may be configured to gradually curve optic fiber 250 from an optic fiber in a first curved position 910 to an optic fiber in a second curved position 920. Illustratively, a compression of actuation structure 620 may be configured to gradually retract optic fiber draw sleeve 850 relative to housing tube 700. In one or more embodiments, a gradual retraction of optic fiber draw sleeve 850 relative to housing tube 700 may be configured to cause optic fiber draw sleeve 850 to apply a compressive force to a portion of housing tube 700, e.g., a first housing tube portion 720. Illustratively, an application of a compressive force to a portion of housing tube 700, e.g., a first housing tube portion 720, may be configured to cause housing tube 700 to gradually curve. In one or more embodiments, a gradual curving of housing tube 700 may be configured to gradually curve optic fiber 250, e.g., from an optic fiber in a first curved position 910 to an optic fiber in a second curved position 920. Illustratively, a line tangent to optic fiber distal end 251 may intersect a line tangent to housing tube proximal end 702 at a second angle, e.g., when optic fiber 250 comprises an optic fiber in a second curved position 920. In one or more embodiments, the second angle may comprise any angle greater than the first angle. For example, the second angle may comprise a 90 degree angle.

Figure 9D:
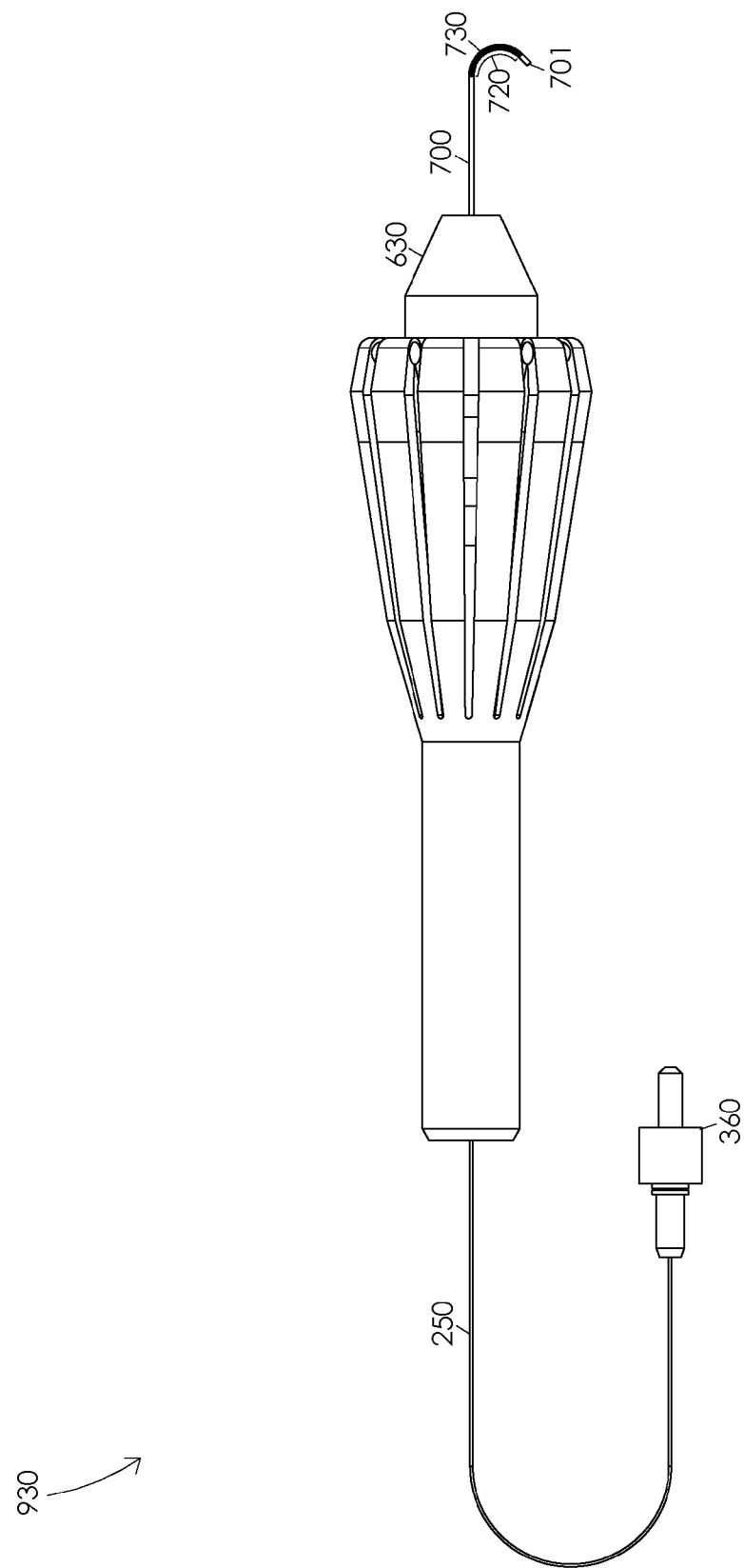

FIG. 9D illustrates an optic fiber in a third curved position 930. In one or more embodiments, a compression of actuation structure 620 may be configured to gradually curve optic fiber 250 from an optic fiber in a second curved position 920 to an optic fiber in a third curved position 930. Illustratively, a compression of actuation structure 620 may be configured to gradually retract optic fiber draw sleeve 850 relative to housing tube 700. In one or more embodiments, a gradual retraction of optic fiber draw sleeve 850 relative to housing tube 700 may be configured to cause optic fiber draw sleeve 850 to apply a compressive force to a portion of housing tube 700, e.g., a first housing tube portion 720. Illustratively, an application of a compressive force to a portion of housing tube 700, e.g., a first housing tube portion 720, may be configured to cause housing tube 700 to gradually curve. In one or more embodiments, a gradual curving of housing tube 700 may be configured to gradually curve optic fiber 250, e.g., from an optic fiber in a second curved position 920 to an optic fiber in a third curved position 930. Illustratively, a line tangent to optic fiber distal end 251 may intersect a line tangent to housing tube proximal end 702 at a third angle, e.g., when optic fiber 250 comprises an optic fiber in a third curved position 930. In one or more embodiments, the third angle may comprise any angle greater than the second angle. For example, the third angle may comprise a 135 degree angle.

Figure 9E:
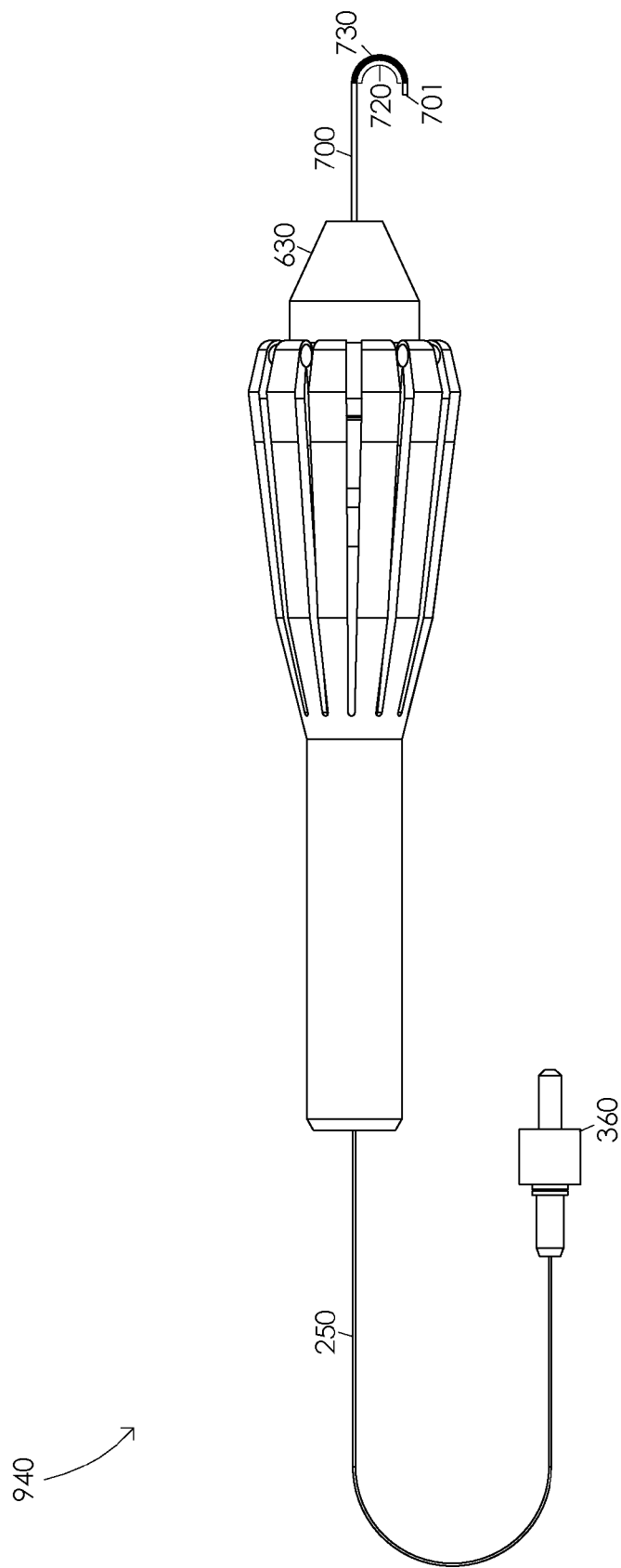

FIG. 9E illustrates an optic fiber in a fourth curved position 940. In one or more embodiments, a compression of actuation structure 620 may be configured to gradually curve optic fiber 250 from an optic fiber in a third curved position 930 to an optic fiber in a fourth curved position 940. Illustratively, a compression of actuation structure 620 may be configured to gradually retract optic fiber draw sleeve 850 relative to housing tube 700. In one or more embodiments, a gradual retraction of optic fiber draw sleeve 850 relative to housing tube 700 may be configured to cause optic fiber draw sleeve 850 to apply a compressive force to a portion of housing tube 700, e.g., a first housing tube portion 720. Illustratively, an application of a compressive force to a portion of housing tube 700, e.g., a first housing tube portion 720, may be configured to cause housing tube 700 to gradually curve. In one or more embodiments, a gradual curving of housing tube 700 may be configured to gradually curve optic fiber 250, e.g., from an optic fiber in a third curved position 930 to an optic fiber in a fourth curved position 940. Illustratively, a line tangent to optic fiber distal end 251 may be parallel to a line tangent to housing tube proximal end 702, e.g., when optic fiber 250 comprises an optic fiber in a fourth curved position 940.

In one or more embodiments, one or more properties of a steerable laser probe may be adjusted to attain one or more desired steerable laser probe features. For example, a length that housing tube 700 extends from housing tube platform 630 may be adjusted to vary an amount of compression of actuation structure 620 configured to curve housing tube 700 to a particular curved position. Illustratively, a length of optic fiber draw sleeve 850 may be adjusted to vary an amount of compression of actuation structure 620 configured to curve housing tube 700 to a particular curved position. In one or more embodiments, a stiffness of optic fiber draw sleeve flexible portion 855 may be adjusted to vary an amount of compression of actuation structure 620 configured to curve housing tube 700 to a particular curved position. Illustratively, a location or a geometry of optic fiber draw sleeve flexible portion 855 may be adjusted to vary an amount of compression of actuation structure 620 configured to curve housing tube 700 to a particular curved position. In one or more embodiments, a stiffness of first housing tube portion 720 or a stiffness of second housing tube portion 730 may be adjusted to vary an amount of compression of actuation structure 620 configured to curve housing tube 700 to a particular curved position. Illustratively, a material comprising first housing tube portion 720 or a material comprising second housing tube portion 730 may be adjusted to vary an amount of compression of actuation structure 620 configured to curve housing tube 700 to a particular curved position.

In one or more embodiments, a number of apertures in housing tube 700 may be adjusted to vary an amount of compression of actuation structure 620 configured to curve housing tube 700 to a particular curved position. Illustratively, a location of one or more apertures in housing tube 700 may be adjusted to vary an amount of compression of actuation structure 620 configured to curve housing tube 700 to a particular curved position. In one or more embodiments, a geometry of one or more apertures in housing tube 700 may be adjusted to vary an amount of compression of action structure 620 configured to curve housing tube 700 to a particular curved position. Illustratively, a geometry of one or more apertures in housing tube 700 may be uniform, e.g., each aperture of the one or more apertures may have a same geometry. In one or more embodiments, a geometry of one or more apertures in housing tube 700 may be non-uniform, e.g., a first aperture in housing tube 700 may have a first geometry and a second aperture in housing tube 700 may have a second geometry.

Illustratively, a distance that handle distal end 601 extends from handle proximal end 602 may be adjusted to vary an amount of compression of actuation structure 620 configured to curve housing tube 700 to a particular curved position. In one or more embodiments, a geometry of actuation structure 620 may be adjusted to vary an amount of compression of actuation structure 620 configured to curve housing tube 700 to a particular curved position. Illustratively, one or more locations within housing tube 700 wherein optic fiber draw sleeve 850 may be fixed to an inner portion of housing tube 700 may be adjusted to vary an amount of compression of actuation structure 620 configured to curve housing tube 700 to a particular curved position. In one or more embodiments, optic fiber draw sleeve 850 may not be included in a steerable laser probe, e.g., a compression of actuation structure 620 may be configured cause optic fiber 250 to apply a force to a portion of housing tube 700 causing housing tube 700 to gradually curve.

Illustratively, a stiffness of first housing tube portion 720 or a stiffness of second housing tube portion 730 may be adjusted to vary a bend radius of housing tube 700. In one or more embodiments, a stiffness of first housing tube portion 720 or a stiffness of second housing tube portion 730 may be adjusted to vary a radius of curvature of housing tube 700, e.g., when housing tube 700 is in a particular curved position. Illustratively, a number of apertures in housing tube 700 may be adjusted to vary a bend radius of housing tube 700. In one or more embodiments, a number of apertures in housing tube 700 may be adjusted to vary a radius of curvature of housing tube 700, e.g., when housing tube 700 is in a particular curved position. Illustratively, a location or a geometry of one or more apertures in housing tube 700 may be adjusted to vary a bend radius of housing tube 700. In one or more embodiments, a location or a geometry of one or more apertures in housing tube 700 may be adjusted to vary a radius of curvature of housing tube 700, e.g., when housing tube 700 is in a particular curved position.

Figure 10A:
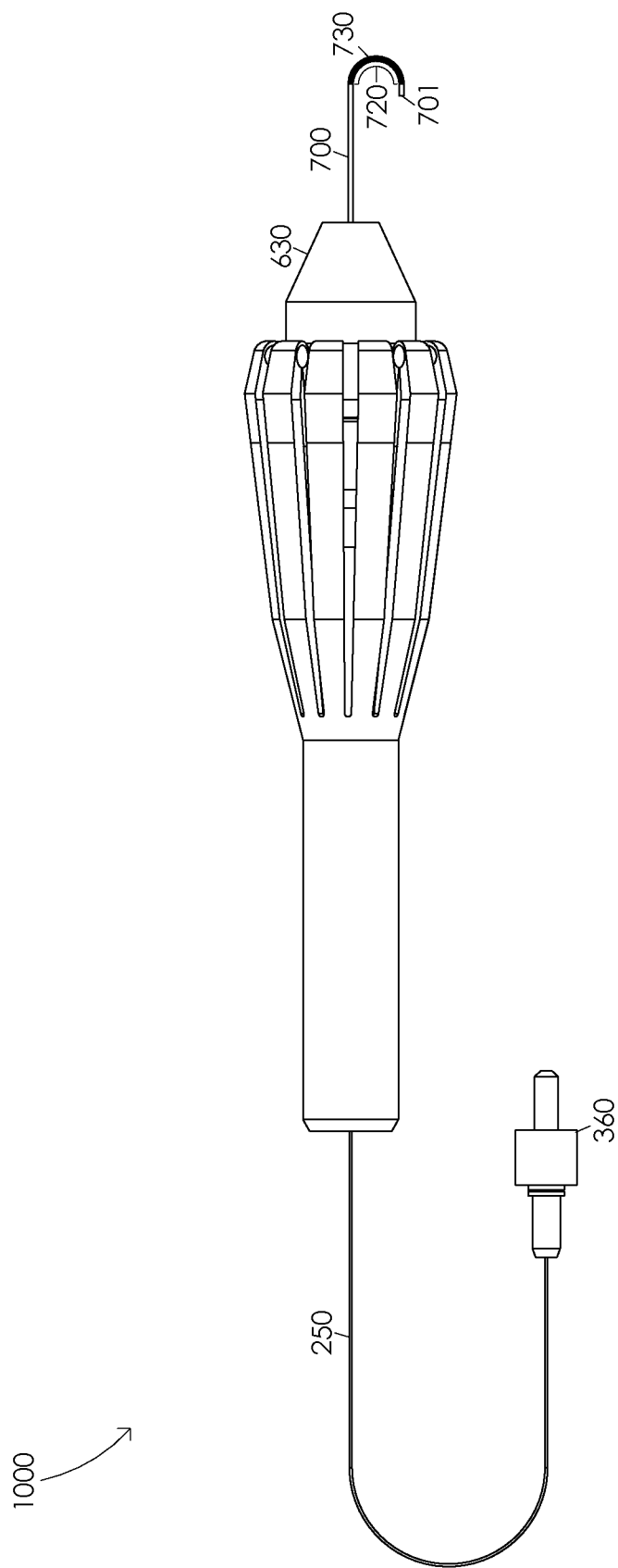
FIGS. 10A, 10B, 10C, 10D, and 10E illustrate a gradual straightening of an optic fiber.

FIGS. 10A, 10B, 10C, 10D, and 10E illustrate a gradual straightening of an optic fiber 250. FIG. 10A illustrates a fully curved optic fiber 1000. In one or more embodiments, optic fiber 250 may comprise a fully curved optic fiber 1000, e.g., when actuation platform 640 is fully retracted relative to handle base 610. Illustratively, optic fiber 250 may comprise a fully curved optic fiber 1000, e.g., when optic fiber draw sleeve 850 is fully retracted relative to housing tube 700. In one or more embodiments, optic fiber 250 may comprise a fully curved optic fiber 1000, e.g., when first housing tube portion 720 is fully compressed. Illustratively, optic fiber 250 may comprise a fully curved optic fiber 1000, e.g., when actuation structure 620 is fully compressed. In one or more embodiments, a line tangent to optic fiber distal end 251 may be parallel to a line tangent to housing tube proximal end 702, e.g., when optic fiber 250 comprises a fully curved optic fiber 1000.

Figure 10B:
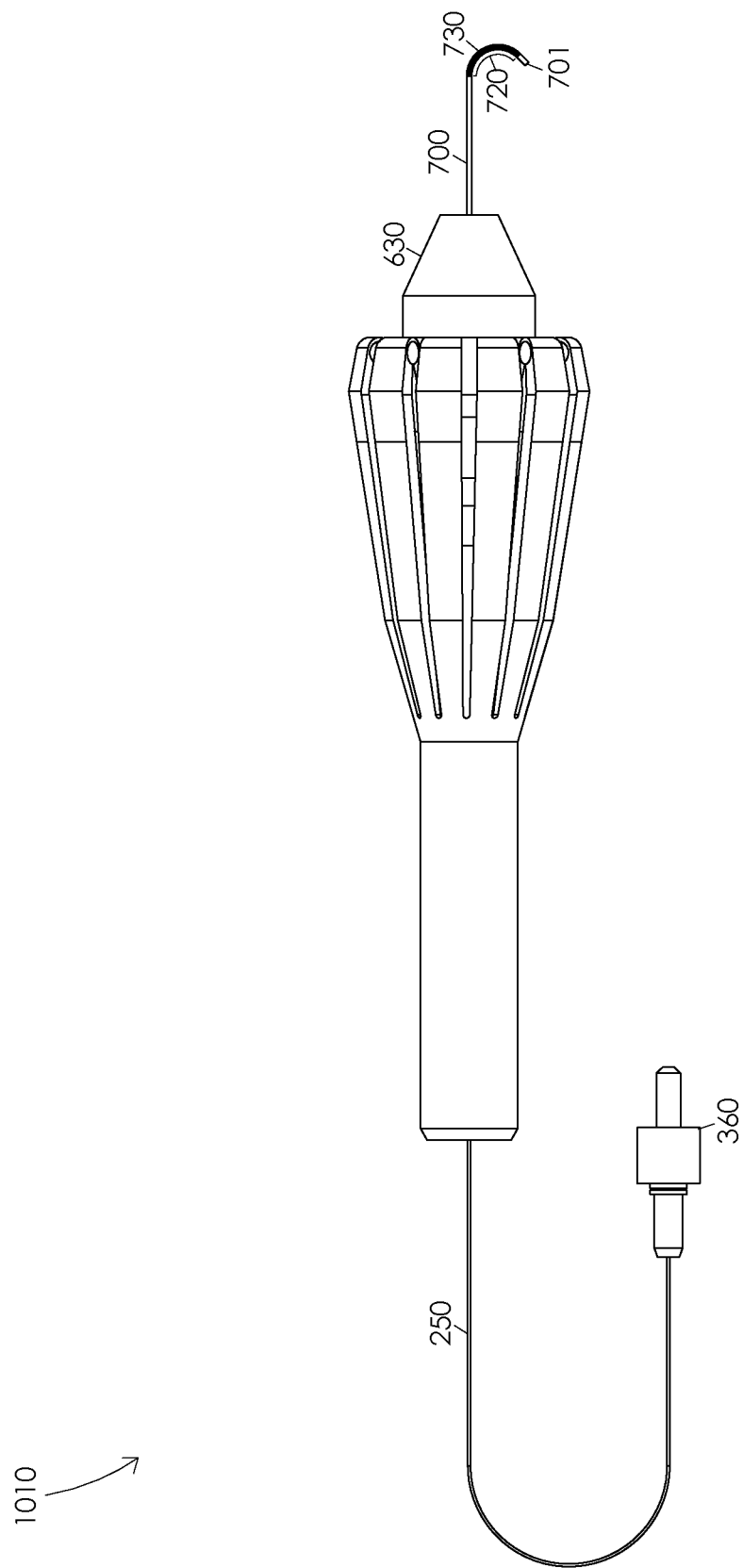

FIG. 10B illustrates an optic fiber in a first partially straightened position 1010. In one or more embodiments, a decompression of actuation structure 620 may be configured to gradually straighten optic fiber 250 from a fully curved optic fiber 1000 to an optic fiber in a first partially straightened position 1010. Illustratively, a decompression of actuation structure 620 may be configured to gradually extend optic fiber draw sleeve 850 relative to housing tube 700. In one or more embodiments, a gradual extension of optic fiber draw sleeve 850 relative to housing tube 700 may be configured to cause optic fiber draw sleeve 850 to reduce a compressive force applied to a portion of housing tube 700, e.g., a first housing tube portion 720. Illustratively, a reduction of a compressive force applied to a portion of housing tube 700, e.g., a first housing tube portion 720, may be configured to cause housing tube 700 to gradually straighten. In one or more embodiments, a gradual straightening of housing tube 700 may be configured to gradually straighten optic fiber 250, e.g., from a fully curved optic fiber 1000 to an optic fiber in a first partially straightened position 1010. Illustratively, a line tangent to optic fiber distal end 251 may intersect a line tangent to housing tube proximal end 702 at a first partially straightened angle, e.g., when optic fiber 250 comprises an optic fiber in a first partially straightened position 1010. In one or more embodiments, the first partially straightened angle may comprise any angle less than 180 degrees. For example, the first partially straightened angle may comprise a 135 degree angle.

Figure 10C:
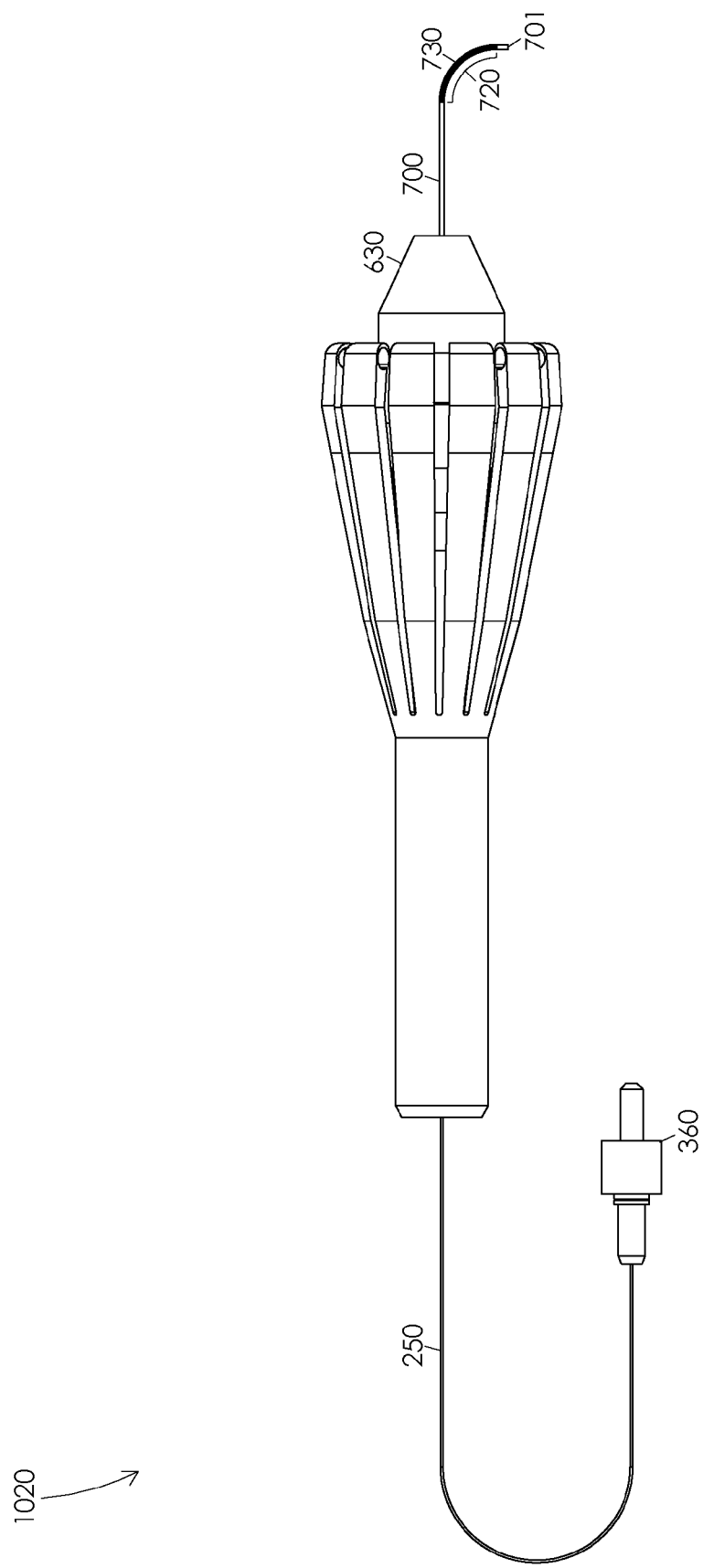

FIG. 10C illustrates an optic fiber in a second partially straightened position 1020. In one or more embodiments, a decompression of actuation structure 620 may be configured to gradually straighten optic fiber 250 from an optic fiber in a first partially straightened position 1010 to an optic fiber in a second partially straightened position 1020. Illustratively, a decompression of actuation structure 620 may be configured to gradually extend optic fiber draw sleeve 850 relative to housing tube 700. In one or more embodiments, a gradual extension of optic fiber draw sleeve 850 relative to housing tube 700 may be configured to cause optic fiber draw sleeve 850 to reduce a compressive force applied to a portion of housing tube 700, e.g., a first housing tube portion 720. Illustratively, a reduction of a compressive force applied to a portion of housing tube 700, e.g., a first housing tube portion 720, may be configured to cause housing tube 700 to gradually straighten. In one or more embodiments, a gradual straightening of housing tube 700 may be configured to gradually straighten optic fiber 250, e.g., from an optic fiber in a first partially straightened position 1010 to an optic fiber in a second partially straightened position 1020. Illustratively, a line tangent to optic fiber distal end 251 may intersect a line tangent to housing tube proximal end 702 at a second partially straightened angle, e.g., when optic fiber 250 comprises an optic fiber in a second partially straightened position 1020. In one or more embodiments, the second partially straightened angle may comprise any angle less than the first partially straightened angle. For example, the second partially straightened angle may comprise a 90 degree angle.

Figure 10D:
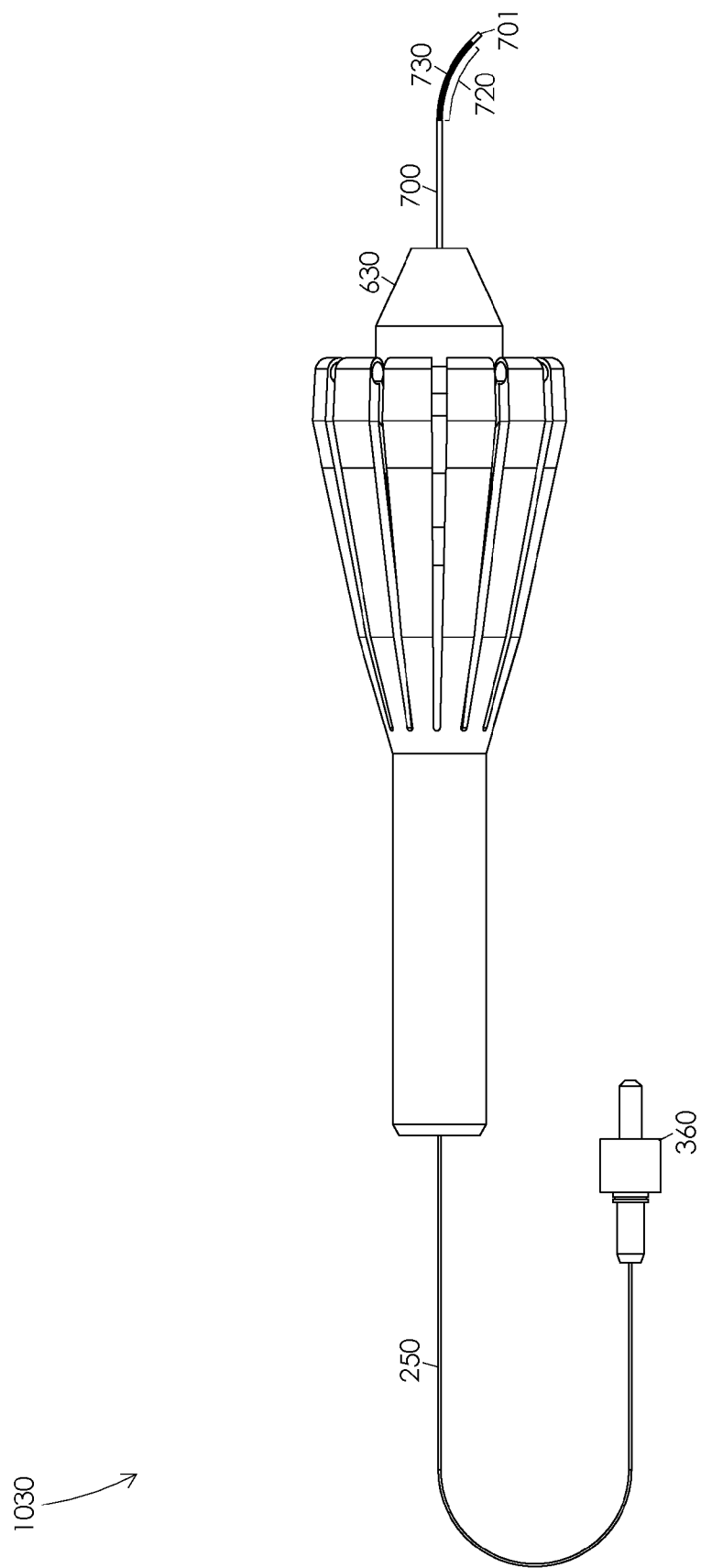

FIG. 10D illustrates an optic fiber in a third partially straightened position 1030. In one or more embodiments, a decompression of actuation structure 620 may be configured to gradually straighten optic fiber 250 from an optic fiber in a second partially straightened position 1020 to an optic fiber in a third partially straightened position 1030. Illustratively, a decompression of actuation structure 620 may be configured to gradually extend optic fiber draw sleeve 850 relative to housing tube 700. In one or more embodiments, a gradual extension of optic fiber draw sleeve 850 relative to housing tube 700 may be configured to cause optic fiber draw sleeve 850 to reduce a compressive force applied to a portion of housing tube 700, e.g., a first housing tube portion 720. Illustratively, a reduction of a compressive force applied to a portion of housing tube 700, e.g., a first housing tube portion 720, may be configured to cause housing tube 700 to gradually straighten. In one or more embodiments, a gradual straightening of housing tube 700 may be configured to gradually straighten optic fiber 250, e.g., from an optic fiber in a second partially straightened position 1020 to an optic fiber in a third partially straightened position 1030. Illustratively, a line tangent to optic fiber distal end 251 may intersect a line tangent to housing tube proximal end 702 at a third partially straightened angle, e.g., when optic fiber 250 comprises an optic fiber in a third partially straightened position 1030. In one or more embodiments, the third partially straightened angle may comprise any angle less than the second partially straightened angle. For example, the third partially straightened angle may comprise a 45 degree angle.

Figure 10E:
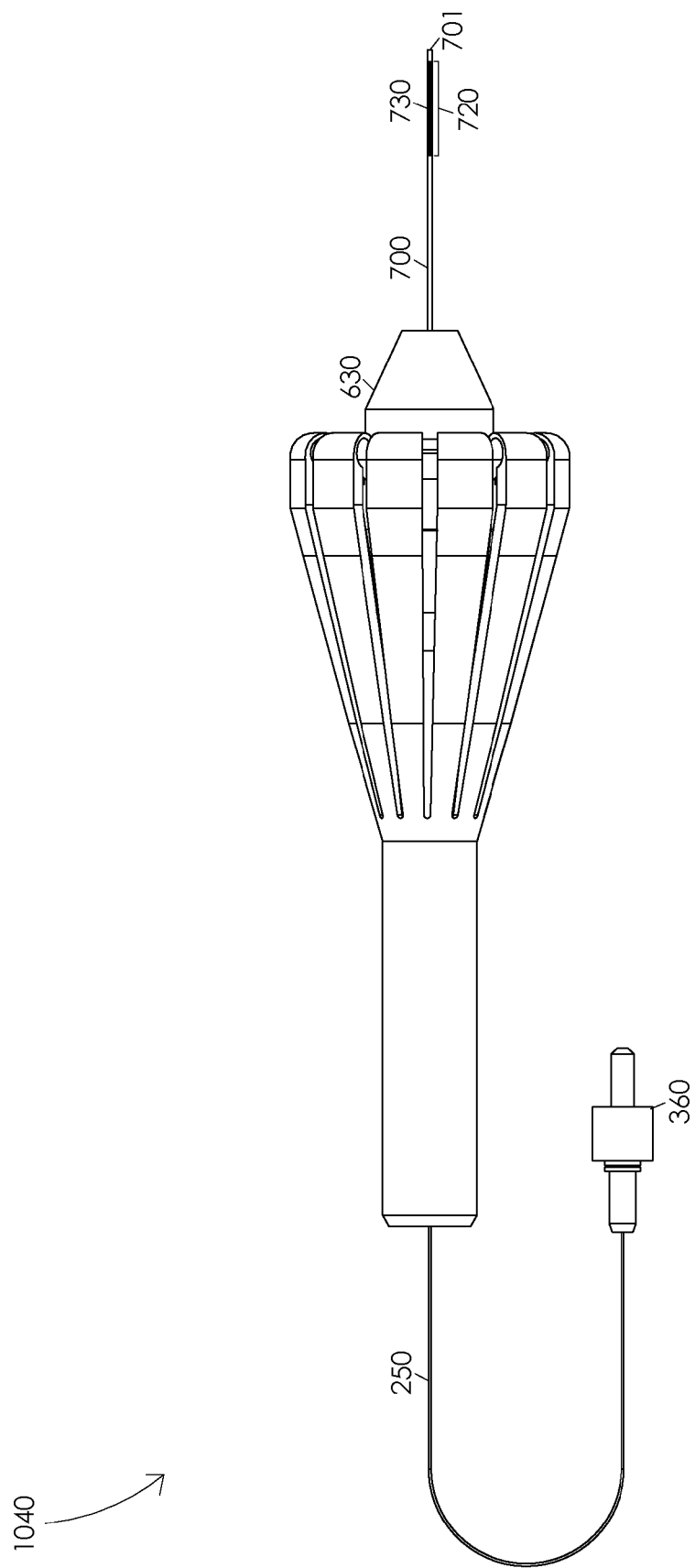

FIG. 10E illustrates an optic fiber in a fully straightened position 1040. In one or more embodiments, a decompression of actuation structure 620 may be configured to gradually straighten optic fiber 250 from an optic fiber in a third partially straightened position 1030 to an optic fiber in a fully straightened position 1040. Illustratively, a decompression of actuation structure 620 may be configured to gradually extend optic fiber draw sleeve 850 relative to housing tube 700. In one or more embodiments, a gradual extension of optic fiber draw sleeve 850 relative to housing tube 700 may be configured to cause optic fiber draw sleeve 850 to reduce a compressive force applied to a portion of housing tube 700, e.g., a first housing tube portion 720. Illustratively, a reduction of a compressive force applied to a portion of housing tube 700, e.g., a first housing tube portion 720, may be configured to cause housing tube 700 to gradually straighten. In one or more embodiments, a gradual straightening of housing tube 700 may be configured to gradually straighten optic fiber 250, e.g., from an optic fiber in a third partially straightened position 1030 to an optic fiber in a fully straightened position 1040. Illustratively, a line tangent to optic fiber distal end 251 may be parallel to a line tangent to housing tube proximal end 702, e.g., when optic fiber 250 comprises an optic fiber in a fully straightened position 1040.

Illustratively, a surgeon may aim optic fiber distal end 251 at any of a plurality of targets within an eye, e.g., to perform a photocoagulation procedure. In one or more embodiments, a surgeon may aim optic fiber distal end 251 at any target within a particular transverse plane of the inner eye by, e.g., rotating handle 600 to orient housing tube 700 in an orientation configured to cause a curvature of housing tube 700 within the particular transverse plane of the inner eye and varying an amount of compression of actuation structure 620. Illustratively, a surgeon may aim optic fiber distal end 251 at any target within a particular sagittal plane of the inner eye by, e.g., rotating handle 600 to orient housing tube 700 in an orientation configured to cause a curvature of housing tube 700 within the particular sagittal plane of the inner eye and varying an amount of compression of actuation structure 620. In one or more embodiments, a surgeon may aim optic fiber distal end 251 at any target within a particular frontal plane of the inner eye by, e.g., varying an amount of compression of actuation structure 620 to orient a line tangent to optic fiber distal end 251 wherein the line tangent to optic fiber distal end 251 is within the particular frontal plane of the inner eye and rotating handle 600. Illustratively, a surgeon may aim optic fiber distal end 251 at any target located outside of the particular transverse plane, the particular sagittal plane, and the particular frontal plane of the inner eye, e.g., by varying a rotational orientation of handle 600 and varying an amount of compression of actuation structure 620. In one or more embodiments, a surgeon may aim optic fiber distal end 251 at any target of a plurality of targets within an eye, e.g., without increasing a length of a portion of a steerable laser probe within the eye. Illustratively, a surgeon may aim optic fiber distal end 251 at any target of a plurality of targets within an eye, e.g., without decreasing a length of a portion of a steerable laser probe within the eye.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any probe system. Furthermore, while this description has been written in terms of a steerable laser probe, the teachings of the present invention are equally suitable to systems where the functionality of actuation may be employed. Therefore, it is the object of the appended claims to cover all such variations and modifications as come within the true spirit and scope of the invention.

What is claimed is:

1. An instrument comprising:
    a handle having a handle distal end and a handle proximal end;
    an actuation structure of the handle;
    a plurality of actuation arms of the actuation structure, each actuation arm of the plurality of actuation arms having at least one extension mechanism;
    an outer nosecone having an outer nosecone distal end and an outer nosecone proximal end;
    a piston tube having a piston tube distal end and a piston tube proximal end, the piston tube distal end fixed to a portion of the outer nosecone;
    an inner nosecone having an inner nosecone distal end and an inner nosecone proximal end, the inner nosecone disposed within the outer nosecone wherein the inner nosecone distal end extends a distance from the outer nosecone distal end;
    a nosecone fixation mechanism configured to fix the inner nosecone within the outer nosecone;
    a housing tube having a housing tube distal end and a housing tube proximal end, the housing tube proximal end disposed within the inner nosecone wherein the housing tube distal end extends out from the inner nosecone distal end and wherein the distance the inner nosecone distal end extends from the outer nosecone distal end is adjustable to vary an amount of compression of the actuation structure configured to curve the housing tube to a particular curved position;
    a first housing tube portion of the housing tube, the first housing tube portion having a first stiffness;
    a second housing tube portion of the housing tube, the second housing tube portion having a second stiffness wherein the second stiffness is greater than the first stiffness;
    an optic fiber sleeve having an optic fiber sleeve distal end, an optic fiber sleeve proximal end, and an optic fiber sleeve flexible portion, the optic fiber sleeve disposed in the handle, an optic fiber sleeve housing of the handle, and the housing tube wherein the optic fiber sleeve is fixed in a position relative to the handle within the optic fiber sleeve housing, the optic fiber sleeve flexible portion is adjacent to the first housing tube portion, and the optic fiber sleeve distal end is fixed to an inner portion of the housing tube; and
    an optic fiber having an optic fiber distal end and an optic fiber proximal end, the optic fiber disposed in an inner bore of the handle, the optic fiber sleeve, and the housing tube wherein the optic fiber distal end extends out from the optic fiber sleeve distal end and the optic fiber distal end is adjacent to the housing tube distal end and wherein the optic fiber is fixed within the housing tube.

2. The instrument of claim 1 wherein a compression of the actuation structure is configured to curve the optic fiber within an eye.

3. The instrument of claim 2 wherein the compression of the actuation structure is configured to curve the optic fiber at least 45 degrees within the eye.

4. The instrument of claim 3 wherein the compression of the actuation structure is configured to curve the optic fiber at least 90 degrees within the eye.

5. The instrument of claim 2 wherein the compression of the actuation structure is configured to curve the optic fiber within the eye without increasing a length of a portion of the instrument within the eye.

6. The instrument of claim 2 wherein the compression of the actuation structure is configured to curve the optic fiber within the eye without decreasing a length of a portion of the instrument within the eye.

7. The instrument of claim 2 wherein the compression of the actuation structure is configured to curve the optic fiber within the eye without increasing a length of a portion of the instrument within the eye and without decreasing the length of the portion of the instrument within the eye.

8. The instrument of claim 1 wherein a decompression of the actuation structure is configured to straighten the optic fiber within an eye.

9. The instrument of claim 8 wherein the decompression of the actuation structure is configured to straighten the optic fiber within the eye without increasing a length of a portion of the instrument within the eye.

10. The instrument of claim 8 wherein the decompression of the actuation structure is configured to straighten the optic fiber within the eye without decreasing a length of a portion of the instrument within the eye.

11. The instrument of claim 8 wherein the decompression of the actuation structure is configured to straighten the optic fiber within the eye without increasing a length of a portion of the instrument within the eye and without decreasing the length of the portion of the instrument within the eye.

* * * * *